United States Patent
Iida et al.

(10) Patent No.: US 12,246,322 B2
(45) Date of Patent: Mar. 11, 2025

(54) MICROSCOPIC OBJECT COLLECTION METHOD AND MICROSCOPIC OBJECT COLLECTION SYSTEM

(71) Applicants: University Public Corporation Osaka, Osaka (JP); Murata Manufacturing Co., Ltd., Nagaokakyo (JP)

(72) Inventors: Takuya Iida, Sakai (JP); Shiho Tokonami, Sakai (JP); Hiroki Ishikawa, Nagaokakyo (JP); Tsutomu Yamasaki, Nagaokakyo (JP)

(73) Assignees: University Public Corporation Osaka, Osaka (JP); MURATA MANUFACTURING CO., LTD., Kyoto (JP)

(*) Notice: Subject to any disclaimer, the term of this patent is extended or adjusted under 35 U.S.C. 154(b) by 700 days.

(21) Appl. No.: 17/606,185

(22) PCT Filed: Apr. 22, 2020

(86) PCT No.: PCT/JP2020/017349
§ 371 (c)(1),
(2) Date: Oct. 25, 2021

(87) PCT Pub. No.: WO2020/218347
PCT Pub. Date: Oct. 29, 2020

(65) Prior Publication Data
US 2022/0226814 A1    Jul. 21, 2022

(30) Foreign Application Priority Data
Apr. 25, 2019   (JP) .................................. 2019-083997

(51) Int. Cl.
*B01L 3/00*      (2006.01)
*B01L 7/00*      (2006.01)
(Continued)

(52) U.S. Cl.
CPC ..... *B01L 3/50851* (2013.01); *B01L 3/502792* (2013.01); *B01L 7/00* (2013.01);
(Continued)

(58) Field of Classification Search
None
See application file for complete search history.

(56) References Cited

U.S. PATENT DOCUMENTS 6,823,124 B1    11/2004   Renn et al.
9,108,196 B1 *   8/2015   Javadi ............... B01L 3/502738
(Continued)

FOREIGN PATENT DOCUMENTS

CN     106546528 A     3/2017
CN     106660004 A     5/2017
(Continued)

OTHER PUBLICATIONS

Office Action in CN202080030848.2, mailed Aug. 3, 2022, 10 pages.
(Continued)

*Primary Examiner* — Brian R Gordon
(74) *Attorney, Agent, or Firm* — Keating & Bennett, LLP

(57) ABSTRACT

A method of collecting resin beads includes first to fourth steps. The first step is a step of preparing a sample on a thin film provided on an upper surface of a substrate. The second step is a step of irradiating the thin film with a laser beam and a laser beam with the laser beam and the laser beam being distant from each other. The third step is a step of producing a microbubble at a position irradiated with the laser beam and producing a microbubble at a position irradiated with the laser beam, by heating the sample by irradiation with the laser beams. The fourth step is a step of collecting a plurality of resin beads in a region between the microbubble and the microbubble by producing convection
(Continued)

of the sample in a direction perpendicular to a direction of alignment of the microbubble and the microbubble.

4 Claims, 28 Drawing Sheets

(51) Int. Cl.
    *G01N 1/18*     (2006.01)
    *G01N 1/40*     (2006.01)
    *G01N 1/44*     (2006.01)
    *G02B 21/32*     (2006.01)

(52) U.S. Cl.
    CPC .............. *G01N 1/18* (2013.01); *G01N 1/4022* (2013.01); *G01N 1/44* (2013.01); *B01L 3/502715* (2013.01); *B01L 2200/0647* (2013.01); *B01L 2300/1861* (2013.01); *G02B 21/32* (2013.01)

(56) References Cited

U.S. PATENT DOCUMENTS

| | | | | |
|---|---|---|---|---|
| 9,364,831 | B2* | 6/2016 | Chiou | F16K 99/0026 |
| 10,620,121 | B2* | 4/2020 | Zheng | G01N 15/14 |
| 10,829,728 | B2* | 11/2020 | Kurz | C12M 23/20 |
| 11,060,976 | B2* | 7/2021 | Zheng | G01N 21/01 |
| 11,612,890 | B2* | 3/2023 | Kurz | B01L 3/502715 422/502 |
| 2001/0030983 | A1 | 10/2001 | Yuri et al. | |
| 2005/0281944 | A1* | 12/2005 | Jang | B05D 1/202 427/180 |
| 2009/0107262 | A1* | 4/2009 | Hashimoto | B01L 3/502738 73/863.11 |
| 2015/0043000 | A1 | 2/2015 | Mochizuki | |
| 2017/0074760 | A1* | 3/2017 | Iida | C12M 1/26 |
| 2017/0082531 | A1 | 3/2017 | Okada et al. | |
| 2018/0065119 | A1* | 3/2018 | Masuhara | B01L 3/502723 |
| 2019/0374944 | A1* | 12/2019 | Lundquist | B01L 7/00 |
| 2019/0383708 | A1* | 12/2019 | Iida | G01N 1/28 |
| 2020/0182770 | A1* | 6/2020 | Tokonami | B25J 7/00 |
| 2021/0339246 | A1* | 11/2021 | Pan | G01N 21/6458 |
| 2022/0184611 | A1* | 6/2022 | Masuhara | B01L 3/50273 |
| 2022/0203370 | A1* | 6/2022 | Choi | B01L 3/502715 |
| 2023/0065504 | A1* | 3/2023 | Wagner | G01N 15/1433 |
| 2023/0080236 | A1* | 3/2023 | Fahmi | G01N 29/348 73/19.03 |
| 2024/0116053 | A1* | 4/2024 | Ho | B01L 3/502761 |
| 2024/0241026 | A1* | 7/2024 | Tokonami | G01N 15/075 |
| 2024/0272157 | A1* | 8/2024 | Iida | G01N 21/6428 |

FOREIGN PATENT DOCUMENTS

| | | |
|---|---|---|
| CN | 108593910 A | 9/2018 |
| CN | 108873294 A | 11/2018 |
| CN | 108998001 A | 12/2018 |
| JP | 2001-284732 A | 10/2001 |
| JP | 2002-219700 A | 8/2002 |
| JP | 2009-049030 A | 3/2009 |
| JP | 2011-062607 A | 3/2011 |
| JP | 2015-035553 A | 2/2015 |
| JP | 2019-056724 A | 4/2019 |
| WO | 2015/170758 A1 | 11/2015 |
| WO | 2017/195872 A1 | 11/2017 |
| WO | 2017/213107 A1 | 12/2017 |
| WO | 2018/159706 A1 | 9/2018 |

OTHER PUBLICATIONS

Official Communication issued in International Patent Application No. PCT/JP2020/017349, mailed on Jul. 21, 2020.

* cited by examiner

<FIRST EMBODIMENT 1>

FIG.2 <COMPARATIVE EXAMPLE>

FIG.20
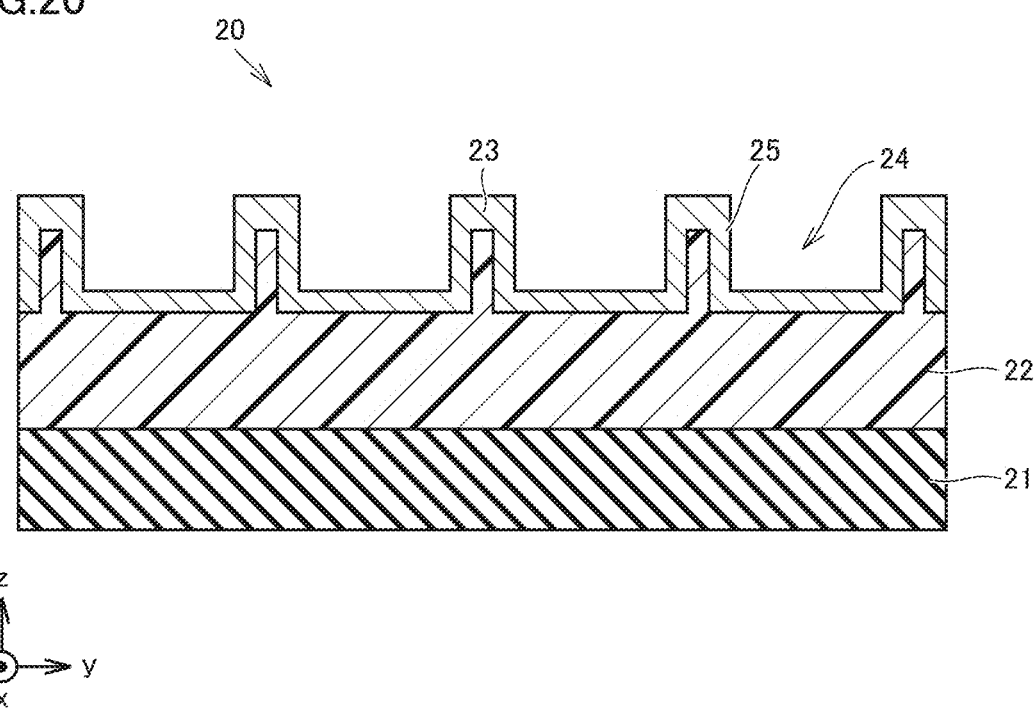
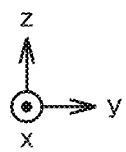

FIG.26 <SECOND EMBODIMENT 2>

MICROSCOPIC OBJECT COLLECTION METHOD AND MICROSCOPIC OBJECT COLLECTION SYSTEM

TECHNICAL FIELD

The present disclosure relates to a microscopic object collection method and a microscopic object collection system, and more particularly to a technique for collecting a plurality of microscopic objects dispersed in a liquid.

BACKGROUND ART

A technique for collecting a plurality of microscopic objects (microparticles, cells, or microorganisms) dispersed in a liquid has been proposed. For example, WO2017/195872 (PTL 1) and WO2018/159706 (PTL 2) each disclose a technique for collecting a plurality of microscopic objects dispersed in a liquid by irradiation with light. As a photothermal conversion region where light is converted to heat is irradiated with light, the liquid in the vicinity of a position irradiated with light is locally heated. A microbubble is thus produced and convection is produced in the liquid. Then, the plurality of microscopic objects are carried by convection to the microbubble and collected in the vicinity of the position irradiated with light.

CITATION LIST

Patent Literature

PTL 1: WO2017/195872
PTL 2: WO2018/159706

SUMMARY OF INVENTION

Technical Problem

A technique for collecting a plurality of microscopic objects dispersed in a liquid by irradiation with light is required to collect more microscopic objects in a shorter period of time, that is, to collect microscopic objects more efficiently.

The present disclosure was made to solve problems above, and an object thereof is to highly efficiently collect a plurality of microscopic objects dispersed in a liquid.

Solution to Problem (1) In a microscopic object collection method according to one aspect of the present disclosure, a plurality of microscopic objects dispersed in a liquid are collected. The microscopic object collection method includes first to fourth steps. The first step is a step of preparing the liquid on a photothermal conversion region provided on a main surface of a substrate. The second step is a step of irradiating the photothermal conversion region with a first beam and a second beam with the first beam and the second beam being distant from each other, the first beam and the second beam each being a beam having a wavelength within an absorption wavelength range of the photothermal conversion region. The third step is a step of producing a first bubble at a position irradiated with the first beam and producing a second bubble at a position irradiated with the second beam by heating the liquid by irradiation with the first and second beams. The fourth step is a step of collecting the plurality of microscopic objects in a region between the first bubble and the second bubble by producing convection of the liquid in a specific direction, the specific direction being a direction in parallel to the main surface and perpendicular to a direction of alignment of the first bubble and the second bubble.

(2) The collecting the plurality of microscopic objects (the fourth step) includes enhancing convection along the specific direction such that a flow velocity of convection along the specific direction is higher than a flow velocity of convection along another direction by setting output of the first and second beams and an interval between the position irradiated with the first beam and the position irradiated with the second beam. Convection along another direction includes convection along the direction in parallel to the main surface and in parallel to the direction of alignment.

(3) The collecting the plurality of microscopic objects (the fourth step) includes producing convection along the specific direction and convection along another direction by setting the output and the interval such that distribution of the plurality of microscopic objects collected around the first bubble is denser on a side of the second bubble in the direction of alignment and distribution of the plurality of microscopic objects collected around the second bubble is denser on a side of the first bubble in the direction of alignment.

(4) The output and the interval are determined based on output and a spot diameter of the first beam, output and a spot diameter of the second beam, and an absorbance and thermal conductivity of the photothermal conversion region.

(5) A microscopic object collection system according to another aspect of the present disclosure collects a plurality of microscopic objects dispersed in a liquid. The microscopic object collection system includes a holder configured to hold a substrate including a main surface provided with a photothermal conversion region and a photoheating apparatus that emits first and second beams, the first and second beams each having a wavelength within an absorption wavelength range of the photothermal conversion region. The photoheating apparatus irradiates the photothermal conversion region with the first beam and the second beam with the first beam and the second beam being distant from each other while the liquid is prepared on the photothermal conversion region. The photoheating apparatus produces a first bubble at a position irradiated with the first beam and a second bubble at a position irradiated with the second beam by heating the liquid by irradiation with the first and second beams. The photoheating apparatus collects the plurality of microscopic objects in a region between the first bubble and the second bubble by producing convection of the liquid in a specific direction, the specific direction being a direction in parallel to the main surface and perpendicular to a direction of alignment of the first bubble and the second bubble.

Advantageous Effects of Invention

According to the present disclosure, a plurality of microscopic objects dispersed in a liquid can highly efficiently be collected.

BRIEF DESCRIPTION OF DRAWINGS

FIG. 20 is a cross-sectional view of the collection kit along the line XX-XX in FIG. 19.

DESCRIPTION OF EMBODIMENTS

Figure 1:
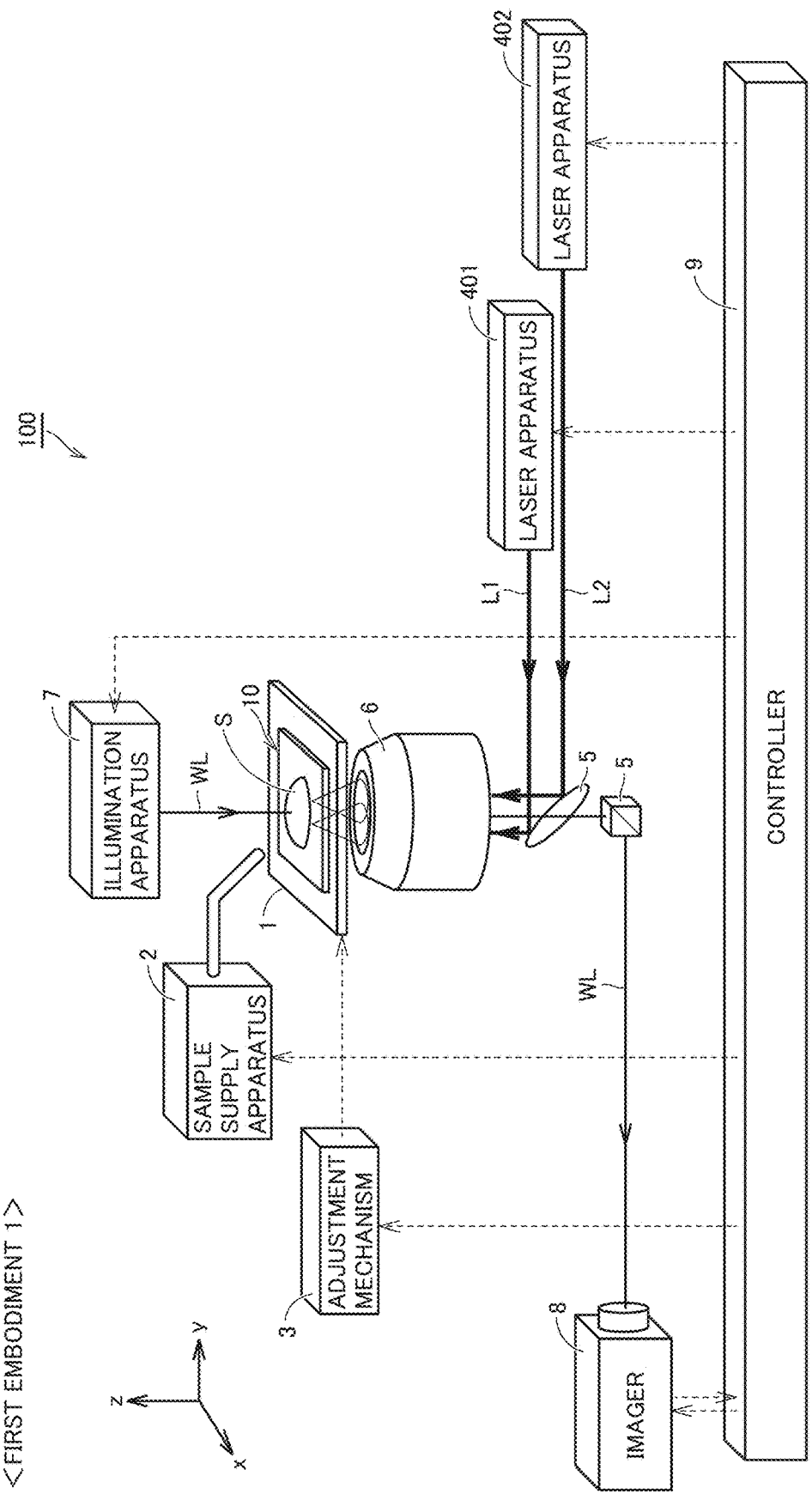
FIG. 1 is a diagram schematically showing an overall configuration of a resin bead collection system according to a first embodiment.

In the present disclosure, a "nanometer order" includes a range from 1 nm to 1000 nm (=1 μm). A "micrometer order" includes a range from 1 μm to 1000 μm (=1 mm). Therefore, a "range from the nanometer order to the micrometer order" includes a range from 1 nm to 1000 μm. The "range from the nanometer order to the micrometer order" may typically represent a range from several nanometers to several hundred micrometers, preferably a range from 100 nm to 100 μm, and more preferably a range from 1 μm to several ten micrometers.

In the present disclosure, the term "microscopic object" means an object having a size within the range from the nanometer order to the micrometer order. A shape of the microscopic object is not particularly limited, and it may be, for example, in a spherical shape, a shape of an oval sphere, or a rod shape (a pole shape). When the microscopic object is in the shape of the oval sphere, at least one of a length in a direction of a major axis and a length in a direction of a minor axis of the oval sphere should only be within the range from the nanometer order to the micrometer order. When the microscopic object is in the rod shape, at least one of a width and a length of the rod should only be within the range from the nanometer order to the micrometer order.

Examples of microscopic objects include a metal nanoparticle, a metal nanoparticle assembly, a metal nanoparticle assembly structure body, a semiconductor nanoparticle, an organic nanoparticle, a resin bead, and a particulate matter (PM). The "metal nanoparticle" refers to a metal particle having a size of the nanometer order. The "metal nanoparticle assembly" refers to an assembly formed by aggregation of a plurality of metal nanoparticles. The "metal nanoparticle assembly structure body" refers, for example, to a structure body in which a plurality of metal nanoparticles are fixed to a surface of a substrate (a resin bead etc.) with an interactive site being interposed and arranged at intervals not larger than a diameter of each metal nanoparticle with gaps being interposed thereamong. The "semiconductor nanoparticle" refers to a semiconductor particle having a size of the nanometer order. The "organic nanoparticle" refers to a particle composed of an organic compound and having a size of the nanometer order. The "resin bead" refers to a particle composed of a resin and having a size within the range from the nanometer order to the micrometer order. The "PM" refers to a particulate substance having a size of the micrometer order. Examples of the PM include PM2.5 and a suspended particulate matter (SPM).

The microscopic object may be a biologically originated substance (a biological substance). More specifically, the microscopic object may include cells, microorganisms (bacteria, fungi, etc.), a biopolymer (protein, nucleic acid, lipid, polysaccharide, etc.), an antigen (allergen etc.), and a virus.

In the present disclosure, the term "honeycomb" means such a shape that a plurality of regular hexagons are disposed two-dimensionally in hexagonal lattices (like a honeycomb). Pores are provided in each of the plurality of regular hexagons. Each pore has an opening within the range from the nanometer order to the micrometer order. The pore may be a through hole or a non-through hole. A shape of the pore is not particularly limited, and the shape may include any shape such as a columnar shape, a prismatic shape, and a spherical shape except for a shape of a true sphere (for example, a hemispherical shape or a shape of a semielliptical sphere). A structure body with a structure in which a plurality of pores are disposed like a honeycomb is referred to as a "honeycomb structure body."

The term "microbubble" in the present disclosure means an air bubble of the micrometer order.

An embodiment of the present disclosure will be described below in detail with reference to the drawings. The same or corresponding elements in the drawings have the same reference characters allotted and description thereof will not be repeated.

First Embodiment

In the first embodiment, resin beads are adopted as one exemplary form of microscopic objects. Polystyrene is adopted as a material for the resin beads. The material for the resin beads is not limited thereto, and acrylic, polyolefin, polyethylene, or polypropylene may be adopted as the material.

An x direction and a y direction represent a horizontal direction below. The x direction and the y direction are orthogonal to each other. A z direction represents a vertical direction. An orientation of the gravity is downward in the z direction. An upward direction in the z direction may be abbreviated as upward and a downward direction in the z direction may be abbreviated as downward.

<Configuration of Collection System>

FIG. 1 is a diagram schematically showing an overall configuration of a resin bead collection system 100 according to the first embodiment. Referring to FIG. 1, collection system 100 includes an XYZ-axis stage 1, a sample supply apparatus 2, an adjustment mechanism 3, laser apparatuses 401 and 402, an optical component 5, an objective lens 6, an illumination apparatus 7, an imager 8, and a controller 9.

XYZ-axis stage 1 is configured to be movable in the x direction, the y direction, and the z direction. XYZ-axis stage 1 holds collection kit 10. A sample S is dropped onto collection kit 10. XYZ-axis stage 1 realizes irradiation with light, of an aimed position of sample S dropped onto collection kit 10. A detailed configuration of collection kit 10 will be described with reference to FIGS. 4 and 5.

Sample supply apparatus 2 supplies liquid sample S onto collection kit 10 in response to an instruction from controller 9. For example, a dispenser can be employed as sample supply apparatus 2.

Adjustment mechanism 3 adjusts a position of XYZ-axis stage 1 in the x direction, the y direction, and the z direction in response to an instruction from controller 9. In the present embodiment, a position of objective lens 6 is fixed. Therefore, relative positional relation between collection kit 10 mounted on XYZ-axis stage 1 and objective lens 6 is adjusted by adjusting the position of XYZ-axis stage 1. Though a drive mechanism (not shown) such as a servo motor and a focusing handle annexed to a microscope can be employed as adjustment mechanism 3, a specific configuration of adjustment mechanism 3 is not particularly limited. Adjustment mechanism 3 may adjust the position of objective lens 6 with respect to fixed collection kit 10.

Laser apparatus 401 emits, for example, a near infrared laser beam L1 in response to an instruction from controller 9. Laser apparatus 402 emits, for example, a near infrared laser beam L2 in response to an instruction from controller 9. A wavelength of laser beams L1 and L2 is not particularly limited so long as the wavelength is within a light absorption band of a material for a thin film 12 (see FIGS. 4 and 5) which will be described later. In the present embodiment, laser beam L1 has a wavelength of 1064 nm and laser beam L2 has a wavelength of 800 nm. The wavelength of laser beam L1 may be equal to the wavelength of laser beam L2.

Optical component 5 includes a mirror, a dichroic mirror, or a prism. An optical system of collection system 100 is adjusted such that optical component 5 guides laser beam L1 from laser apparatus 401 to objective lens 6 and guides laser beam L2 from laser apparatus 402 to objective lens 6.

Laser apparatuses 401 and 402 and optical component 5 correspond to the "photoheating apparatus" according to the present disclosure. It is not essential, however, that the "photoheating apparatus" includes two laser apparatuses. The photoheating apparatus may split a laser beam emitted from a single laser apparatus into two beams, for example, by means of a half mirror.

Objective lens 6 condenses laser beam L1 from laser apparatus 401 and condenses laser beam L2 from laser apparatus 402. Sample S on collection kit 10 is irradiated with light condensed by objective lens 6. A beam waist of light condensed by objective lens 6 may be located out of sample S. Optical component 5 and objective lens 6 can be incorporated in a main body of an inverted or erect microscope.

Illumination apparatus 7 emits white light WL for irradiating sample S within collection kit 10 in response to an instruction from controller 9. In one example, a halogen lamp can be employed as illumination apparatus 7. Objective lens 6 is used also for taking in white light WL emitted from illumination apparatus 7 to collection kit 10. White light WL taken in by objective lens 6 is guided to imager 8 by optical component 5.

Imager 8 takes an image of sample S on collection kit 10 irradiated with white light WL in response to an instruction from controller 9 and provides the taken image to controller 9. A video camera including charge coupled device (CCD) image sensors or complementary metal oxide semiconductor (CMOS) image sensors is employed as imager 8. Illumination apparatus 7 and imager 8 are merely devices for taking an image of a state of sample S and they are not constituent elements essential for collection of resin beads by collection system 100.

Controller 9 controls each device (sample supply apparatus 2, adjustment mechanism 3, laser apparatuses 401 and 402, illumination apparatus 7, and imager 8) included in collection system 100. Controller 9 is implemented by a microcomputer including a processor such as a central processing unit (CPU), a memory such as a read only memory (ROM) and a random access memory (RAM), and an input and output port (none of which is shown).

For facilitated understanding of features of collection system 100 according to the first embodiment, description will be given below with collection system 100 being compared with a collection system 900 according to a comparative example.

Figure 2:
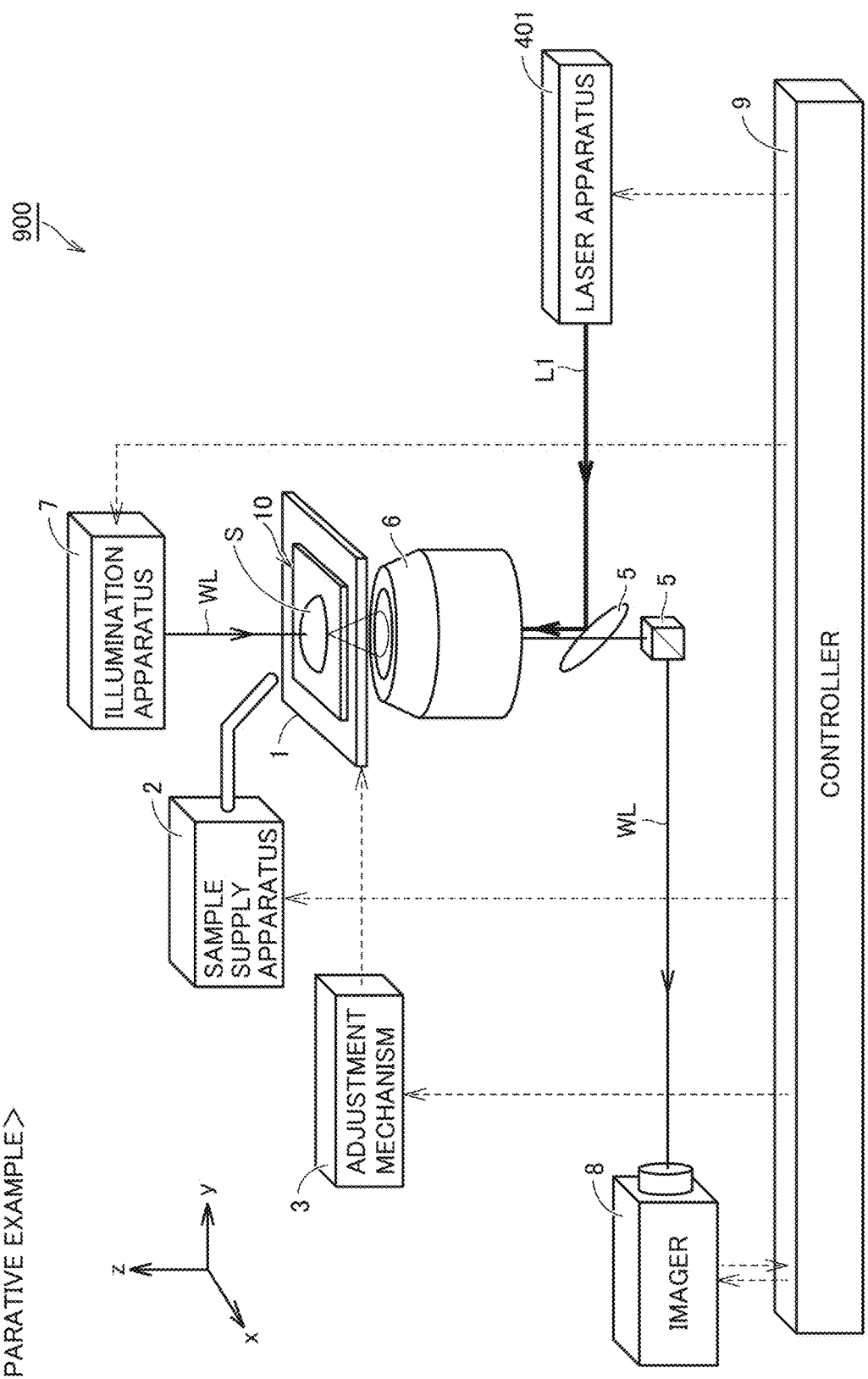
FIG. 2 is a diagram schematically showing an overall configuration of a resin bead collection system according to a comparative example.

FIG. 2 is a diagram schematically showing an overall configuration of resin bead collection system 900 according to the comparative example. Referring to FIG. 2, collection system 900 according to the comparative example is different from collection system 100 (see FIG. 1) according to the first embodiment in not including laser apparatus 402. The configuration of collection system 900 is otherwise similar to the corresponding configuration of collection system 100. Collection kit 10 is in common between collection systems 100 and 900.

Figure 3:
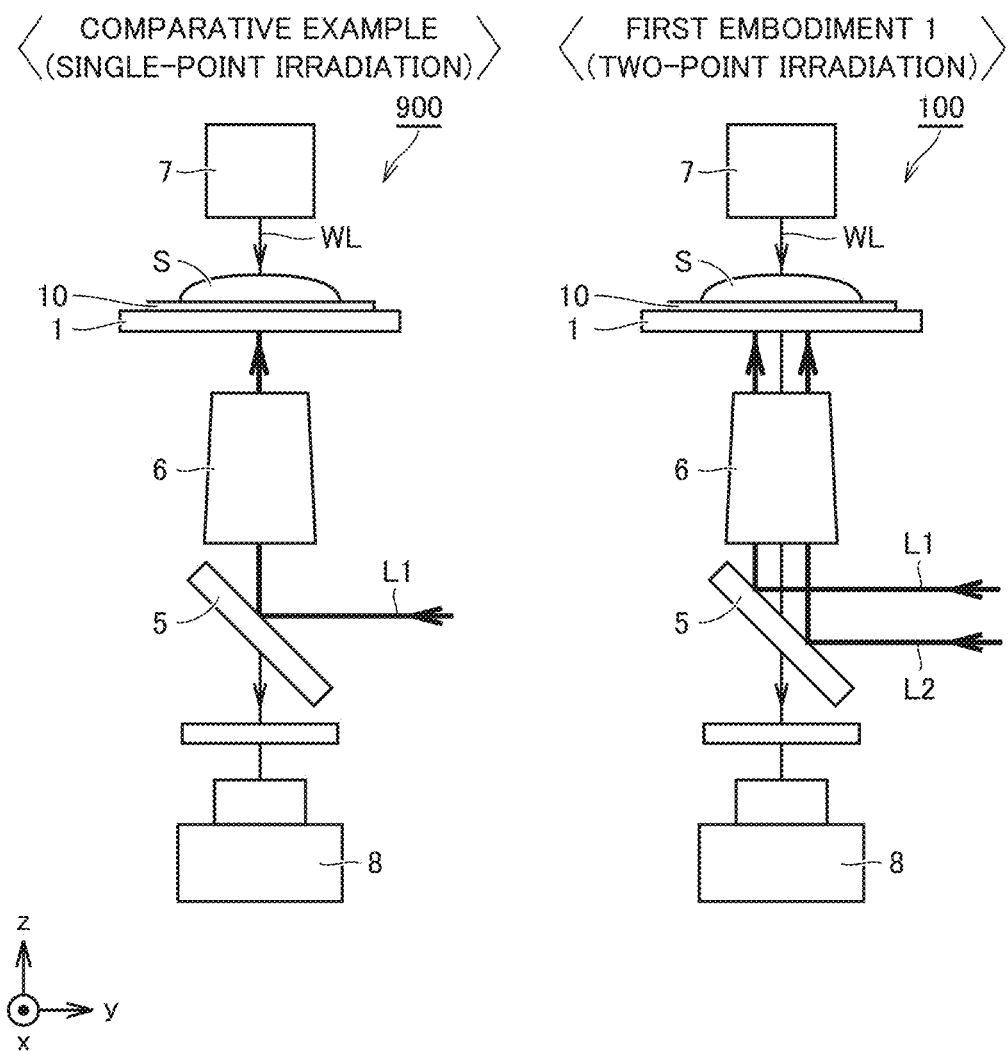
FIG. 3 is a diagram for illustrating an optical system of the collection system according to the first embodiment and an optical system of the collection system according to the comparative example.

FIG. 3 is a diagram for illustrating an optical system of collection system 100 according to the first embodiment and an optical system of collection system 900 according to the comparative example. In an example shown in FIG. 3, in each of collection systems 100 and 900, sample S is dropped onto collection kit 10 held on XYZ-axis stage 1. Illumination apparatus 7 is arranged above XYZ-axis stage 1. Objective lens 6, optical component 5, and imager 8 are arranged below XYZ-axis stage 1.

In collection system 900 according to the comparative example, optical component 5 shown in FIG. 3 is a dichroic mirror, and it reflects near infrared light whereas it transmits white light. Optical component 5 reflects near infrared laser beam L1 emitted horizontally from laser apparatus 401 and guides the laser beam to objective lens 6 above optical component 5. Objective lens 6 condenses laser beam L1 from below. Sample S further above objective lens 6 is irradiated with condensed light. White light WL from illumination apparatus 7 passes through sample S downward from above and further passes through objective lens 6 and optical component 5 to be guided to imager 8. Imager 8 thus takes an image of a state around a position irradiated with laser beam L1 (a laser spot).

In collection system 100 according to the first embodiment, laser beam L1 from laser apparatus 401 is condensed by objective lens 6, and in addition, laser beam L2 from laser apparatus 402 is condensed by objective lens 6. Then, sample S is irradiated with two beams of condensed light. Thus, collection system 900 is a system for irradiation of a single point with light, whereas collection system 100 is a system for irradiation of two points with light. A manner of irradiation with light in the comparative example is also referred to as "single-point irradiation" below and a manner of irradiation with light in the first embodiment is also referred to as "two-point irradiation" below.

The optical system of collection system 100 is not limited to the configuration shown in FIG. 1 so long as the optical system can emit laser beams L1 and L2 to collection kit 10 and can take white light WL from collection kit 10 into imager 8. The optical system of collection system 100 may be configured, for example, to emit laser beams L1 and L2 downward from above or may include another optical component 5 such as optical fibers.

<Configuration of Collection Kit>

Figure 4:
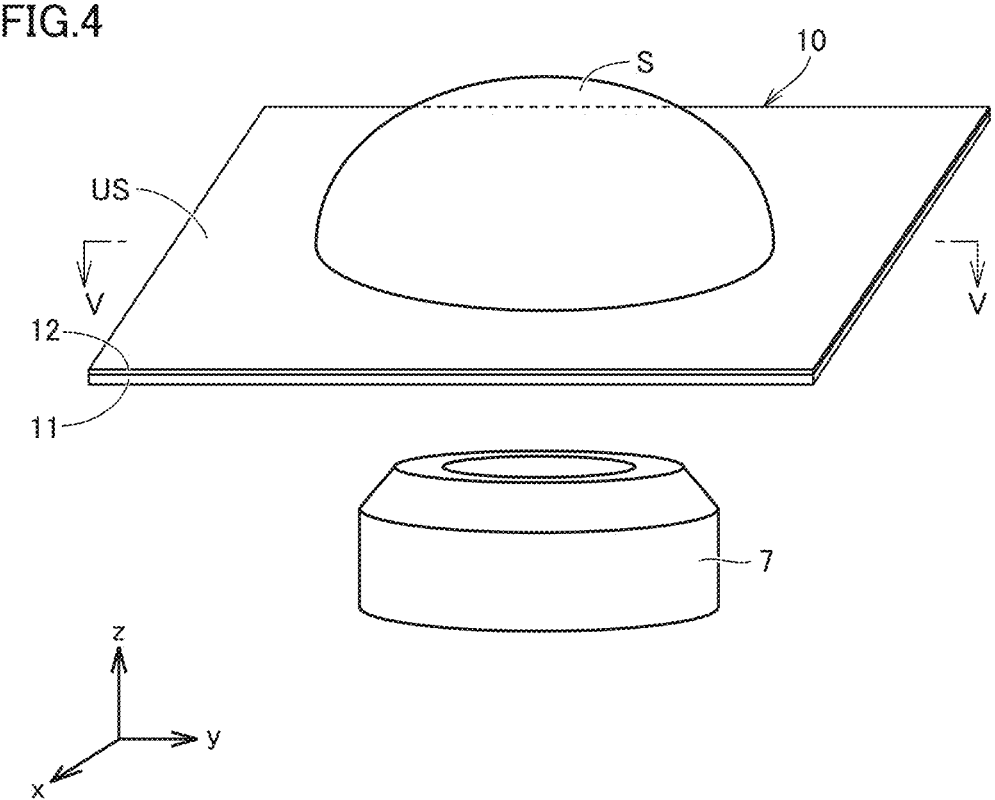
FIG. 4 is a perspective view schematically showing a configuration of a collection kit.
Figure 5:
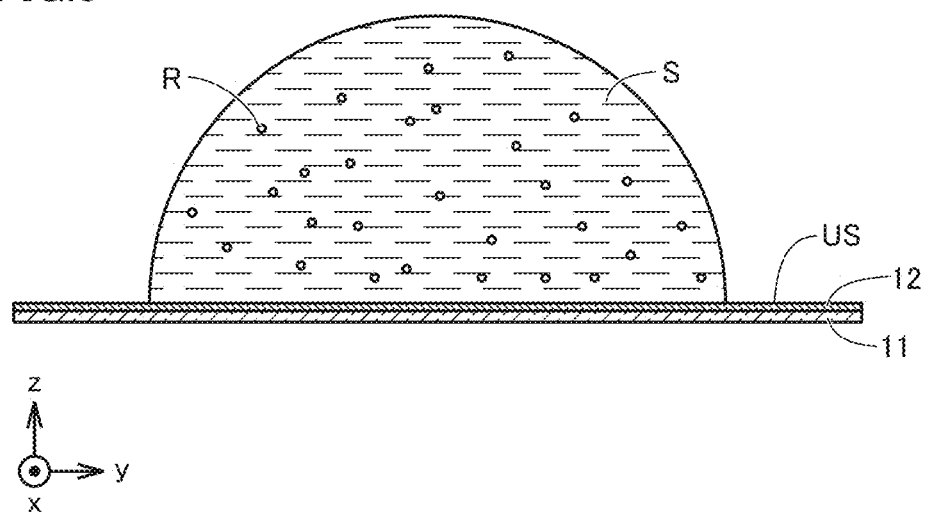
FIG. 5 is a cross-sectional view of the collection kit along the line V-V in FIG. 4.

FIG. 4 is a perspective view schematically showing a configuration of collection kit 10. FIG. 5 is a cross-sectional view of collection kit 10 along the line V-V in FIG. 4. FIG. 4 does not show XYZ-axis stage 1.

Referring to FIGS. 4 and 5, collection kit 10 is in a shape of a flat plate. Sample S is dropped on an upper surface US in this shape of the flat plate. Upper surface US of collection kit 10 corresponds to the "main surface" according to the present disclosure.

Sample S is a liquid in which resin beads R are dispersed. Though a type of a liquid (dispersion medium) is not particularly limited, water is adopted as the liquid in this example. A non-ionic surfactant for expediting collection of resin beads R are added to sample S (see PTL 2 for details of a function of the surfactant).

Collection kit 10 includes a substrate 11 and thin film 12. Substrate 11 is formed of a material that does not affect photothermal conversion (which will be described later) of laser beams L1 and L2 by thin film 12 and is transparent to white light WL. Examples of such a material include quartz and silicon. In the first embodiment, a glass substrate (cover glass) is employed as substrate 11.

Thin film 12 absorbs laser beam L1 from laser apparatus 401 and laser beam L2 from laser light source 402 and converts light energy into thermal energy. A material for thin film 12 is preferably high in photothermal conversion efficiency in a wavelength range (the near infrared region in the present embodiment) of laser beams L1 and L2. In the first embodiment, a gold thin film having a thickness of the nanometer order (specifically, for example, 10 nm) is formed as thin film 12. The gold thin film can be formed by using a known method such as sputtering or electroless plating. Thin film 12 does not have to be formed on the entire surface of substrate 11 but should only be formed on at least a part of substrate 11.

When the gold thin film is formed as thin film 12, free electrons at a surface of the gold thin film form surface plasmons and are oscillated by laser beams L1 and L2. Polarization thus occurs. Energy of this polarization is converted to energy of lattice vibration as a result of Coulomb interaction between free electrons and nuclei. Consequently, the gold thin film generates heat. This effect is also referred to as a "photothermal effect" below.

The material for thin film 12 is not limited to gold, and a metal element (for example, silver) other than gold or a metal nanoparticle assembly structure body (for example, a structure body containing gold nanoparticles or silver nanoparticles) that may achieve the photothermal effect may be applicable. Alternatively, the material for thin film 12 may be a material other than a metal high in light absorption factor in the wavelength range of laser beams L1 and L2. Examples of such a material include a material close to a black body (for example, a carbon nanotube black body). A thickness of thin film 12 is determined in terms of design or experimentally, taking into account laser output as well as an absorption wavelength range and photothermal conversion efficiency of the material for thin film 12. Thin film 12 corresponds to the "photothermal conversion region" according to the present disclosure.

A shape of collection kit 10 is not limited to the shape of the flat plate. Collection kit 10 may be a container in which an internal space for holding sample S is defined. Specifically, a columnar glass bottom dish can be employed as collection kit 10. The gold thin film can be formed on the bottom surface of the glass bottom dish (see PTL 2). In this case, a bottom surface of the glass bottom dish corresponds to the "substrate" according to the present disclosure.

<Collection Flow>

Figure 6:
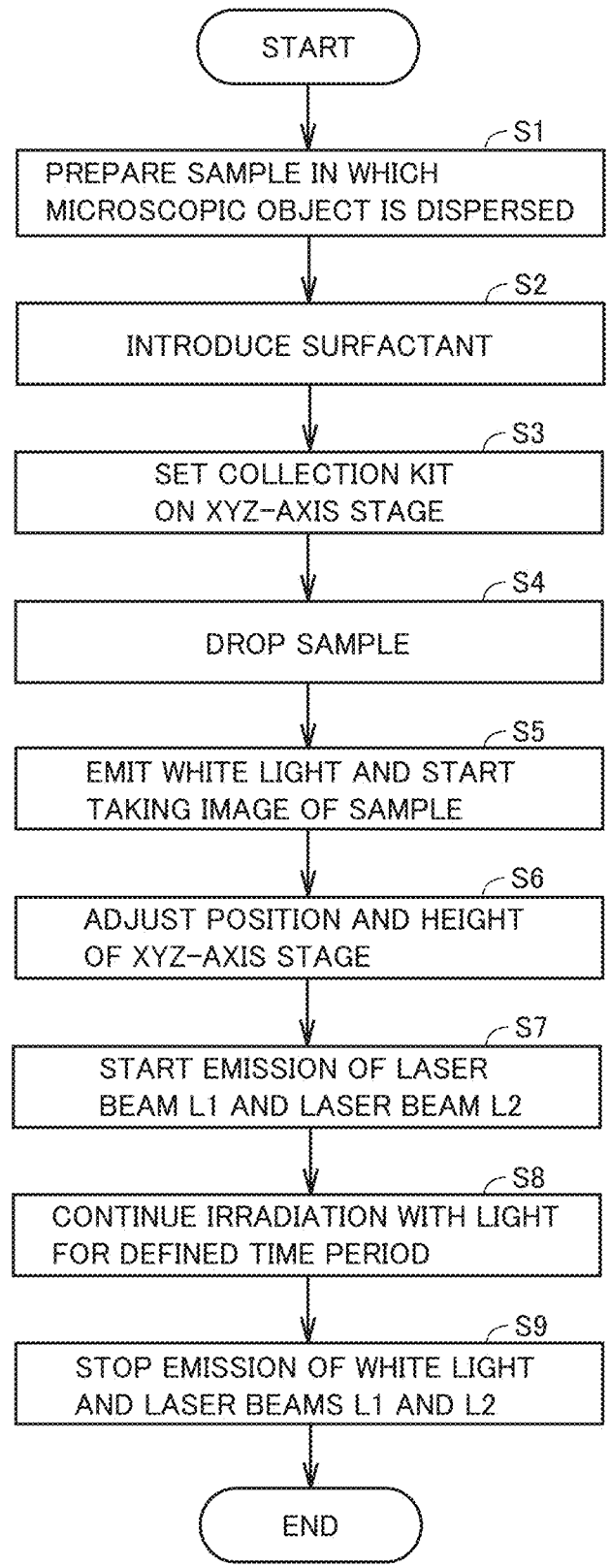
FIG. 6 is a flowchart showing a method of collecting resin beads in the first embodiment.

FIG. 6 is a flowchart showing a method of collecting resin beads R in the first embodiment. Though each step after step S3 is basically performed by software processing by controller 9 in this flowchart, a part or the entirety thereof may be performed by hardware (electric circuitry) made in controller 9. A method of collecting resin beads R in the comparative example is also common.

Referring to FIG. 6, in step S1, sample S in which resin beads R are dispersed is prepared. A surfactant is introduced into sample S (step S2). Introduction of the surfactant, however, is not essential. Sample S prepared in steps S1 and S2 is stored in sample supply apparatus 2.

In step S3, controller 9 has collection kit 10 set on XYZ-axis stage 1. This processing can be realized, for example, by a substrate feed mechanism (not shown) provided in collection system 100.

In step S4, controller 9 controls sample supply apparatus 2 to drop an appropriate amount of sample S onto collection kit 10. An amount of dropped sample S may be, for example, a trace amount from several microliters to several hundred microliters or an amount larger than that.

In step S5, controller 9 controls illumination apparatus 7 to emit white light WL for irradiation of sample S. Controller 9 controls imager 8 to start taking an image of sample S. Processing in step S5 is processing for observing sample S and not essential for collection of resin beads R.

In step S6, controller 9 controls adjustment mechanism 3 to adjust a horizontal position and a height (a vertical position) of XYZ-axis stage 1 such that an aimed region of sample S is irradiated with laser beams L1 and L2. Specifically, controller 9 can obtain a horizontal position of sample S by extracting an outer geometrical pattern of sample S with the use of an image processing technique for pattern recognition from the image taken by imager 8. Then, controller 9 adjusts the horizontal position of XYZ-axis stage 1 as appropriate from an initial position to thereby set a horizontal position of irradiation with laser beams L1 and L2 to an aimed position in sample S. A vertical position of a focus (beam waist) of laser beams L1 and L2 has already been known from the wavelengths of laser beams L1 and L2 and specifications (a magnification etc.) of objective lens 6. Therefore, controller 9 can set a height of the beam waist of laser beams L1 and L2 to an aimed height in sample S by adjusting the height of XYZ-axis stage 1 from an initial height as appropriate.

In step S7, controller 9 controls laser apparatus 401 to start emission of laser beam L1 and controls laser apparatus 402 to start emission of laser beam L2. Timing to start emission of laser beams L1 and L2 may be the same or different. In measurement examples (see FIGS. 10 to 14 and 21 to 25) which will be described later, timing to start emission of laser beams L1 and L2 is the same.

In step S8, controller 9 continues irradiation of collection kit 10 with laser beams L1 and L2 for a defined time period. The defined time period is, for example, approximately from several ten seconds to several minutes, and it is determined in advance by a user. With this irradiation with light, resin beads R are collected.

In step S9, controller 9 controls laser apparatuses 401 and 402 to stop irradiation of collection kit 10 with laser beams L1 and L2. Controller 9 controls illumination apparatus 7 to stop irradiation of collection kit 10 with white light WL. A series of processing thus ends.

<Collection Mechanism>

Figure 7:
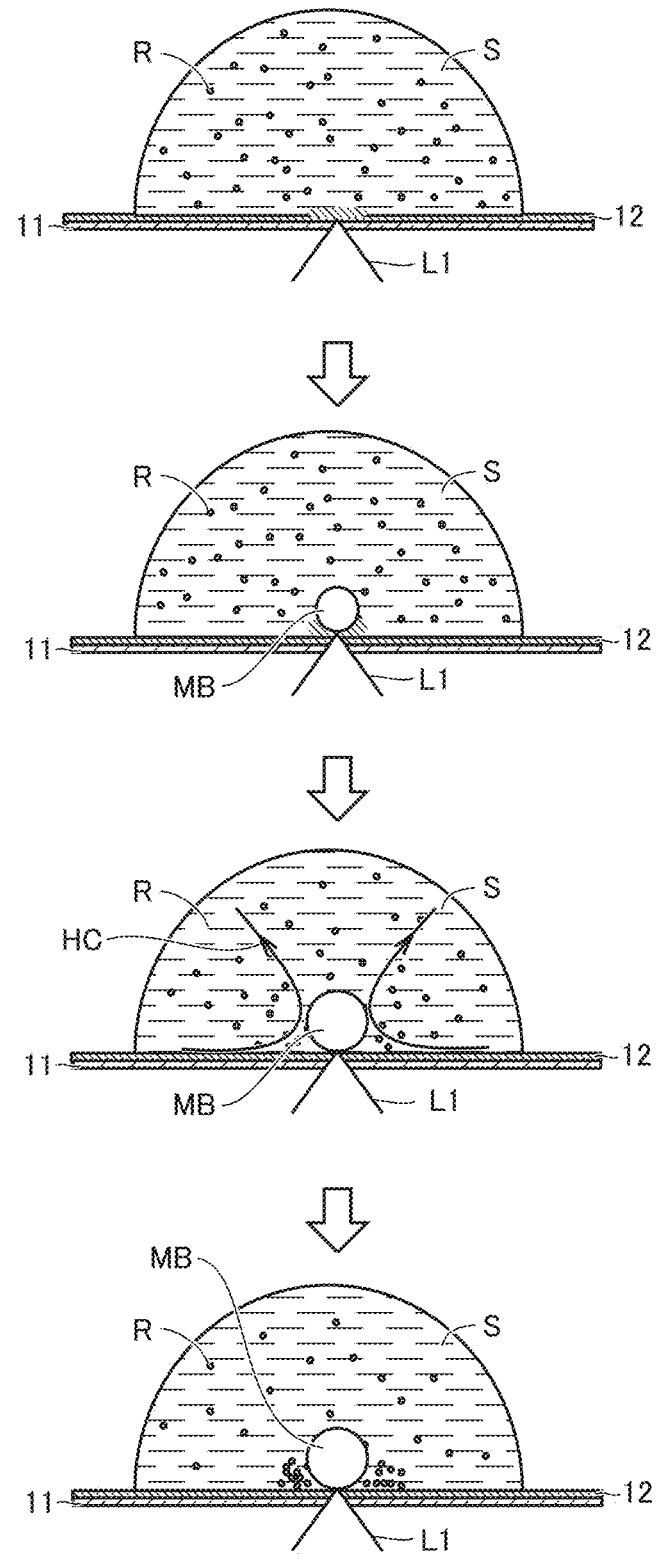
FIG. 7 is a diagram for illustrating a resin bead collection mechanism by single-point irradiation.

FIG. 7 is a diagram for illustrating a mechanism for collecting resin beads R by single-point irradiation. Referring to FIG. 7, as emission of laser beam L1 is started, a portion in the vicinity of a laser spot is locally heated owing to the photothermal effect of thin film 12 at the laser spot. Consequently, a dispersion medium of sample S in the vicinity of the laser spot boils and a microbubble MB is produced at the laser spot. Microbubble MB grows over time.

As a position is closer to the laser spot, a temperature of the dispersion medium is higher. In other words, a temperature gradient is produced in the dispersion medium as a result of irradiation with light. Regular heat convection (buoyant convection) is steadily produced in the dispersion medium due to this temperature gradient. A direction of heat convection produced in single-point irradiation is a direction once heading toward microbubble MB and thereafter deviating from microbubble MB as shown with a reference character HC.

Reasons for production of such heat convection can be explained as below. The dispersion medium present above a region where microbubble MB is produced is relatively leaner as a result of heating and moves upward owing to buoyancy. Concurrently, the dispersion medium at a relatively low temperature present horizontally to microbubble MB flows toward microbubble MB.

Resin beads R are carried over heat convection toward microbubble MB and collected in the vicinity of the laser spot. More specifically, a region where a flow velocity of convection is substantially zero (which is also referred to a "stagnation region" below) is produced between microbubble MB and thin film 12. Resin beads R carried over heat convection build up in the stagnation region and are collected therein. When irradiation with laser beam L1 is stopped thereafter, heat convection becomes weaker and soon stops.

Figure 8:
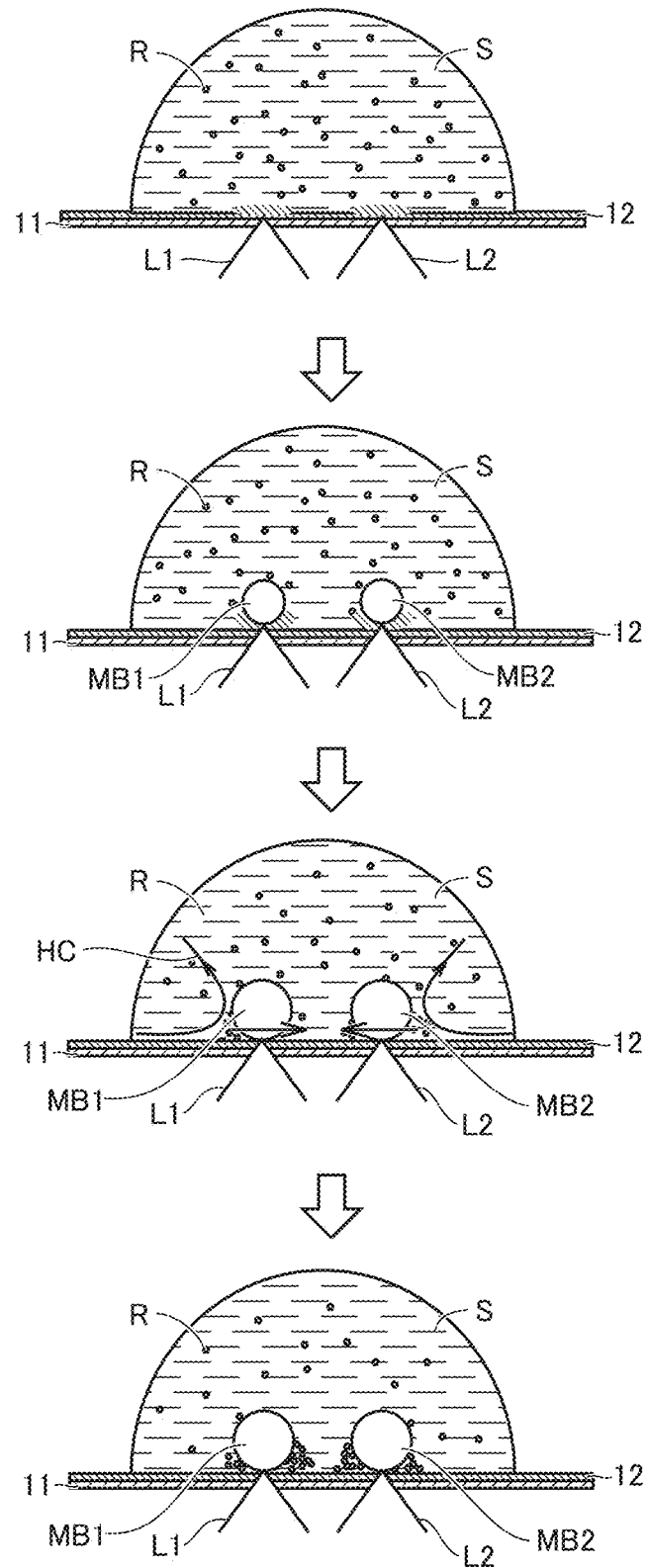
FIG. 8 is a diagram for illustrating overview of the resin bead collection mechanism by two-point irradiation.

FIG. 8 is a diagram for illustrating overview of the mechanism for collecting resin beads R by two-point irradiation. This figure illustrates in further detail, contents in processing included in step S8. Referring to FIG. 8, in two-point irradiation, a microbubble MB1 is produced as a result of irradiation with laser beam L1 and a microbubble MB2 is produced by irradiation with laser beam L2. In two-point irradiation as well, resin beads R are carried by heat convection, build up in the stagnation region around each of microbubbles MB1 and MB2, and are collected. Details of the collection mechanism will be described later.

<Result of Collection of Resin Beads>

Figure 9:
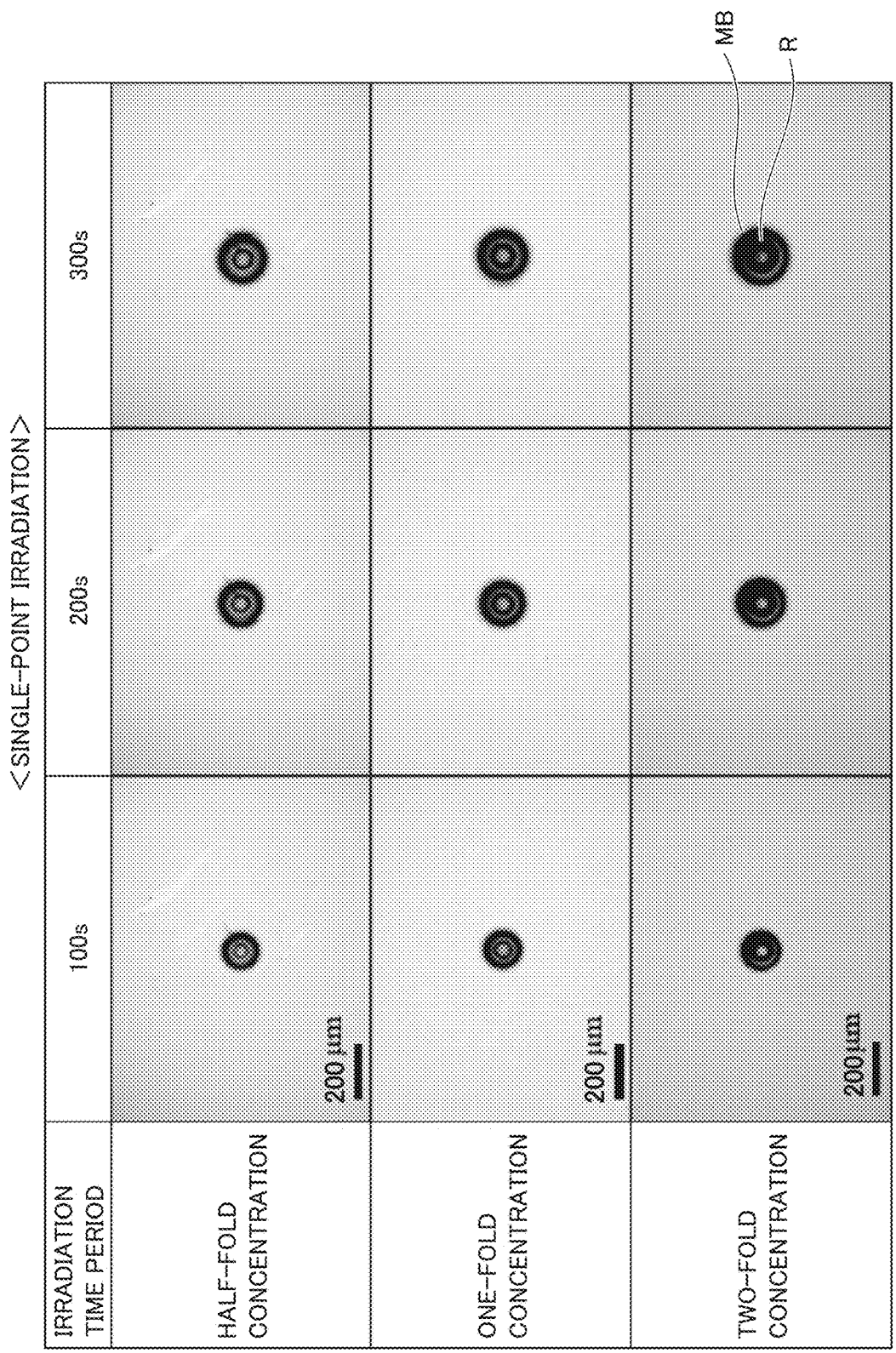
FIG. 9 is a diagram showing an exemplary result of collection of resin beads by single-point irradiation.
Figure 10:
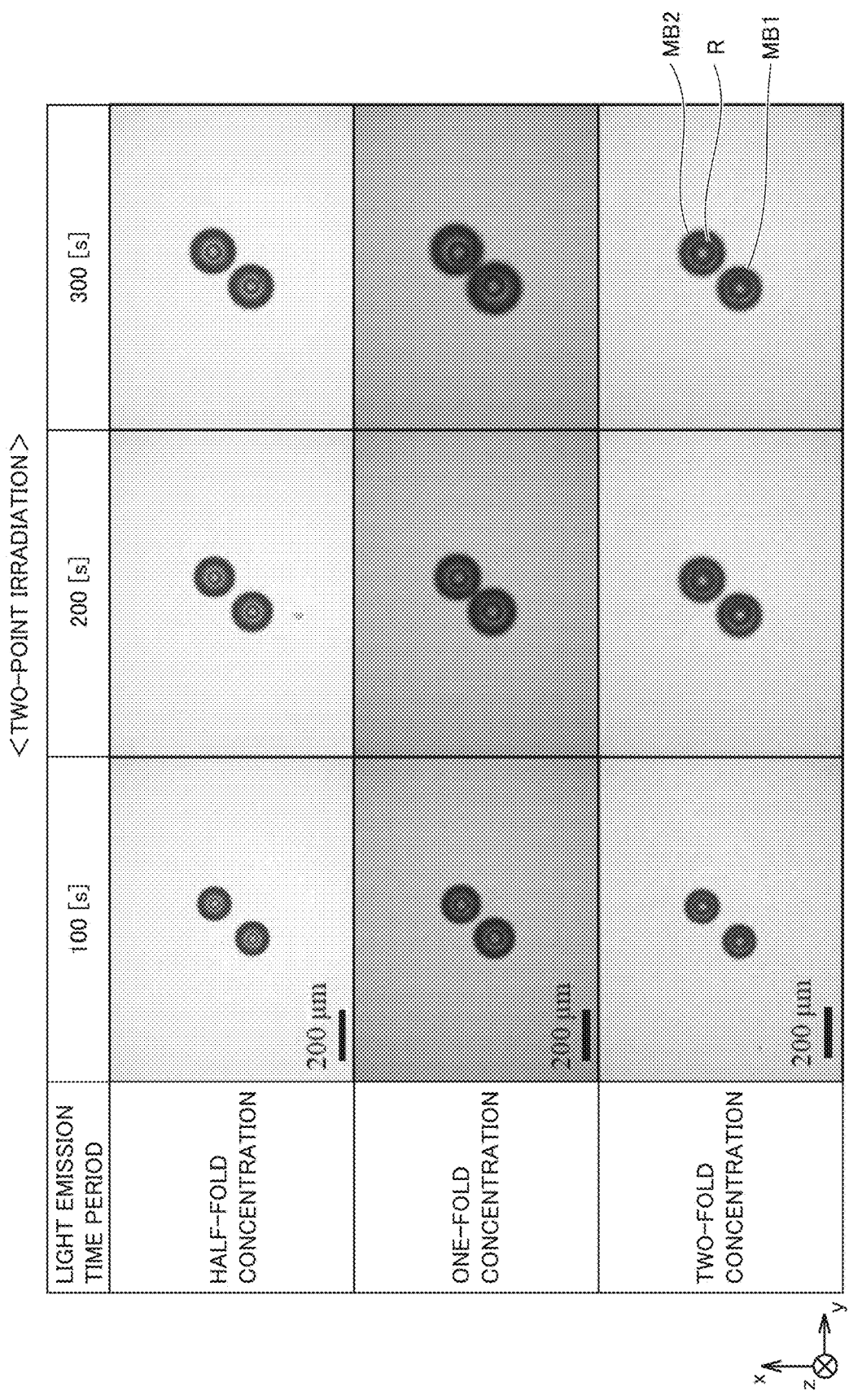
FIG. 10 is a diagram showing an exemplary result of collection of resin beads by two-point irradiation.

FIG. 9 is a diagram showing an exemplary result of collection of resin beads R by single-point irradiation. FIG. 10 is a diagram showing an exemplary result of collection of resin beads R by two-point irradiation. FIGS. 9 and 10 each show consecutive images showing a manner of collection of resin beads R after lapse of 100 seconds, 200 seconds, and 300 seconds since start of irradiation with light. In this example, timing to start irradiation of two points (with laser beams L1 and L2) was the same. These images were obtained by taking images of collection kit 10 from below as described previously.

Resin bead R had a diameter of 1.0 μm. Sample S had a volume of 10 μL. Preparations were made to set a concentration of resin beads R in three patterns of half-fold, one-fold, and two-fold, with $1.01 \times 10^8$ (particles/mL) being defined as the reference. Tween®20 was employed as the surfactant. A concentration of the surfactant was $4.52 \times 10^{-5}$ (mol/L).

A numerical aperture (NA) of objective lens 6 was 0.30. A laser spot had a diameter of 10.4 μm. An interval between two laser spots was 160 μm. A diameter of the laser spot is also denoted as a "spot diameter" below, and an interval between two laser spots is also denoted as a "spot interval G" below. Spot interval G is preferably larger than the sum of two spot diameters (that is, two laser spots are separate from each other). When the objective lens is of one hundred magnifications, the spot diameter is set, for example, to 1.0 μm. When the objective lens is of forty magnifications, the spot diameter is set to 2.5 μm. When the objective lens is of ten magnifications, the spot diameter is set to 10 μm.

In single-point irradiation, output of laser beam L1 after passage through collection kit 10 was set to 100 mW. In two-point irradiation, output of laser beam L1 after passage through collection kit 10 and output of laser beam L2 after passage through collection kit 10 were both set to 50 mW. In other words, a condition was set such that total output of laser beam L1 and laser beam L2 in two-point irradiation was equal to output of laser beam L1 in single-point irradiation.

Referring to FIG. 9, in single-point irradiation, microbubble MB was produced in the vicinity of a single laser spot. In two-point irradiation, as shown in FIG. 10, microbubbles MB1 and MB2 were produced in the vicinity of two respective laser spots. In each of single-point irradiation and two-point irradiation, resin beads R were collected in the stagnation region produced between the microbubble and thin film 12. With lapse of time since start of irradiation with light, the microbubble increased in size and the number of resin beads R (the number of collected resin beads) collected in the stagnation region also increased. The number of collected resin beads R increased as the concentration of resin beads R was higher.

The number of collected resin beads R can be calculated as below. Initially, a contour of a region where resin beads R are collected is extracted by edge detection from the images shown in FIGS. 9 and 10. Then, an area where resin beads R were collected (an area of projection onto a surface of collection kit 10) is calculated based on the extracted contour. A volume of collected resin beads R corresponding to the area where resin beads R were collected is geometrically calculated. More specifically, a space lying between a sphere representing the microbubble and a plane representing upper surface US of collection kit 10 is defined by reading a diameter of the microbubble from the image. By multiplying the volume of the defined space by a fill factor 0.74 of a closest-packed structure, the total of volumes of collected resin beads R (a volume of collected resin beads R) can be calculated. The number of collected resin beads R is calculated by dividing the volume of collected resin beads R by a volume per resin bead R.

Figure 11:
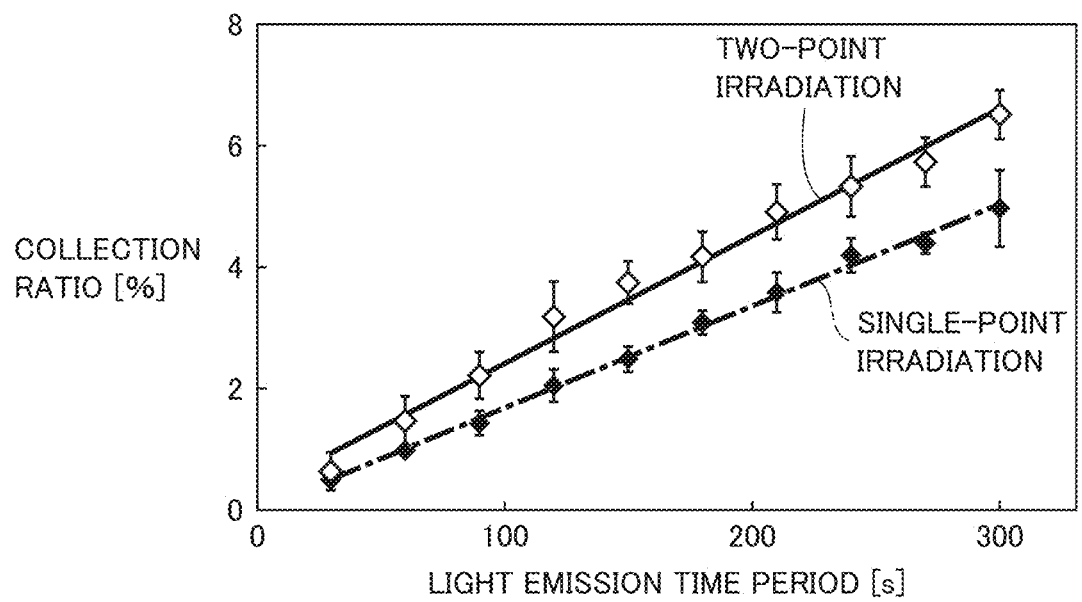
FIG. 11 is a diagram for comparison between single-point irradiation and two-point irradiation, of how collection of resin beads R proceeds by irradiation with light.

FIG. 11 is a diagram for comparison between single-point irradiation and two-point irradiation, of how collection of resin beads R proceeds by irradiation with light. In FIG. 11, the abscissa represents elapsed time since start of irradiation with light and the ordinate represents a ratio of collection of resin beads R. The ratio of collection of resin beads R refers to a ratio of the number of collected resin beads R to the total number of resin beads R included in sample S (the collection ratio=100×the number of collected resin beads/the total number).

Referring to FIG. 11, in each of single-point irradiation and two-point irradiation, with lapse of time since start of irradiation with light, the ratio of collection of resin beads R linearly increased. Based on comparison at identical time, the ratio of collection of resin beads R by two-point irradiation was higher than the ratio of collection of resin beads R by single-point irradiation, and was approximately 1.4 time higher. Thus, even when total output of laser beams L1 and L2 in two-point irradiation is equal to output of laser beam L1 in single-point irradiation, two-point irradiation can achieve the improved ratio of collection of resin beads R as compared with single-point irradiation.

Figure 12:
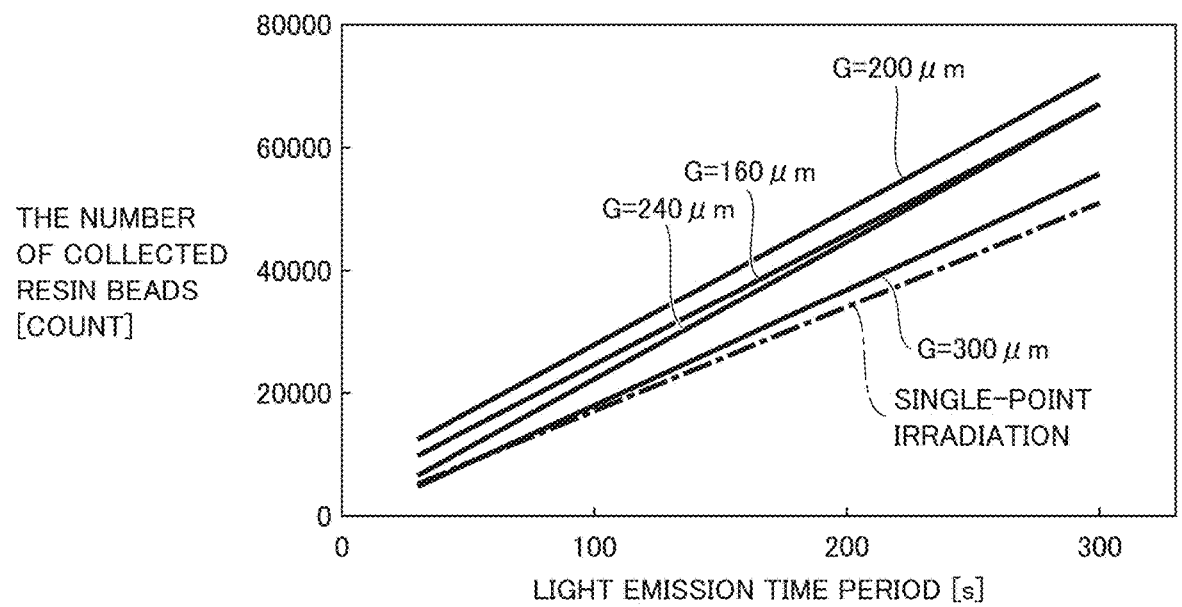
FIG. 12 is a diagram showing dependency on a spot interval, of the number of collected resin beads by two-point irradiation.

FIG. 12 is a diagram showing dependency on a spot interval, of the number of collected resin beads R by two-point irradiation. In FIG. 12, the abscissa represents time elapsed since start of irradiation with laser beams L1 and L2 and the ordinate represents the number of collected resin beads R. In this example, four spot intervals G (160 μm, 200 μm, 240 μm, and 300 μm) were set, and change over time in number of collected resin beads R at each spot interval G was measured. The numerical aperture of objective lens 6 was 0.30. FIG. 12 also shows change over time in number of collected resin beads R in single-point irradiation for comparison.

The number of collected resin beads R was larger in two-point irradiation than in single-point irradiation at each of four spot intervals G. In the example shown in FIG. 12, the number of collected resin beads R was largest when spot interval G was set to 200 μm.

Thus, there is an optimal value of spot interval G at which the number of collected microscopic objects can be maximized, depending on a spot diameter of laser beams L1 and L2 and characteristics (absorbance and heat conduction) of thin film 12. Therefore, desirably, a value as close as possible to the optimal value is determined experimentally or in terms of design within a range where the spot interval is longer than ½ the sum of the spot diameter of laser beam L1 and the spot diameter of laser beam L2 so as to avoid overlapping of two laser spots with each other, and that value is set. Output of laser beams L1 and L2 is also desirably similarly set to a value as close as possible to the optimal value, depending on the spot diameters of laser beams L1 and L2 and characteristics of thin film 12.

<Trace of Resin Beads>

In order to find out a cause of improvement in ratio of collection of resin beads R in two-point irradiation, the present inventors conducted experiments to take images of a plurality of resin beads R. Then, the present inventors analyzed taken moving images (actual measurement images) and tracked motion of resin beads R over a horizontal plane (an xy plane). A trace of resin beads R reflects an orientation and magnitude (velocity) of convection.

Figure 13:
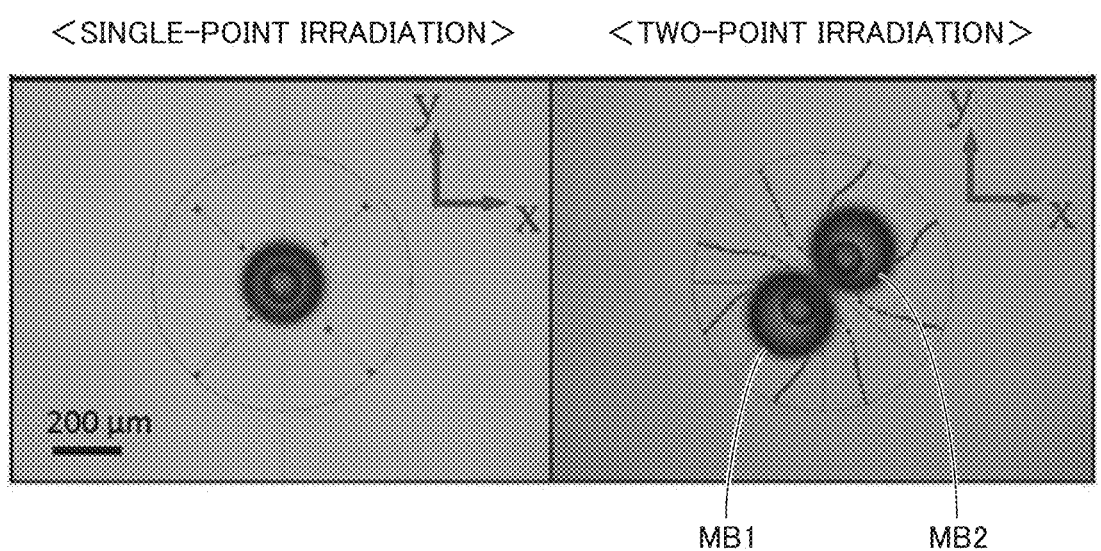
FIG. 13 is a diagram for illustrating an orientation of convection found from an actual measurement image.

FIG. 13 is a diagram for illustrating an orientation of convection found from an actual measurement image. Referring to FIG. 13, on the left in the figure, a trace of resin beads R found from a result of experiments in single-point irradiation is shown as being superimposed on an enlarged image showing a result of collection of resin beads R by single-point irradiation. On the right in the figure, a trace of resin beads R found from a result of experiments in two-point irradiation is shown as being superimposed on an enlarged image showing a result of collection of resin beads R by two-point irradiation.

Initially, with attention being paid to the enlarged image of the result of collection of resin beads R, in single-point irradiation, the laser spot is located at the center of the image (an intersection of two straight lines drawn in a quadrangular image) and resin beads R are evenly collected around the laser spot.

In contrast, in two-point irradiation, a point intermediate between two laser spots is located at the center of the image. At this time, collection of resin beads R denser toward the center of the image relative to each laser spot is observed. In other words, in a direction of alignment of two microbubbles MB1 and MB2, more resin beads R are collected in a region on an inner side of the center of microbubble MB1 and on an inner side of the center of microbubble MB2 than in a region on an outer side of the center of microbubble MB1 and on an outer side of the center of microbubble MB2.

A result of analysis of the trace will be described in succession. In single-point irradiation, irradiation with laser beam L1 was started from a state in which a plurality of (four in this example) resin beads R were located on a circumference having a radius of 300 μm around the laser spot. In two-point irradiation, irradiation with laser beams L1 and L2 was started from a state in which a plurality of (eight in this example) resin beads R were located on a circumference having a radius of 300 μm around a point intermediate between two laser spots.

In each of single-point irradiation and two-point irradiation, as irradiation with light is started, each of the plurality of resin beads R starts moving toward the laser spot. The trace of each resin bead R in single-point irradiation is linear toward the laser spot, which indicates production of convection in point symmetry with respect to microbubble MB in single-point irradiation. In contrast, in two-point irradiation, the trace of each resin bead R is curved toward to a portion between two laser spots. It can thus be seen that convection toward a region between microbubble MB1 and microbubble MB2 is produced in two-point irradiation.

Figure 14:
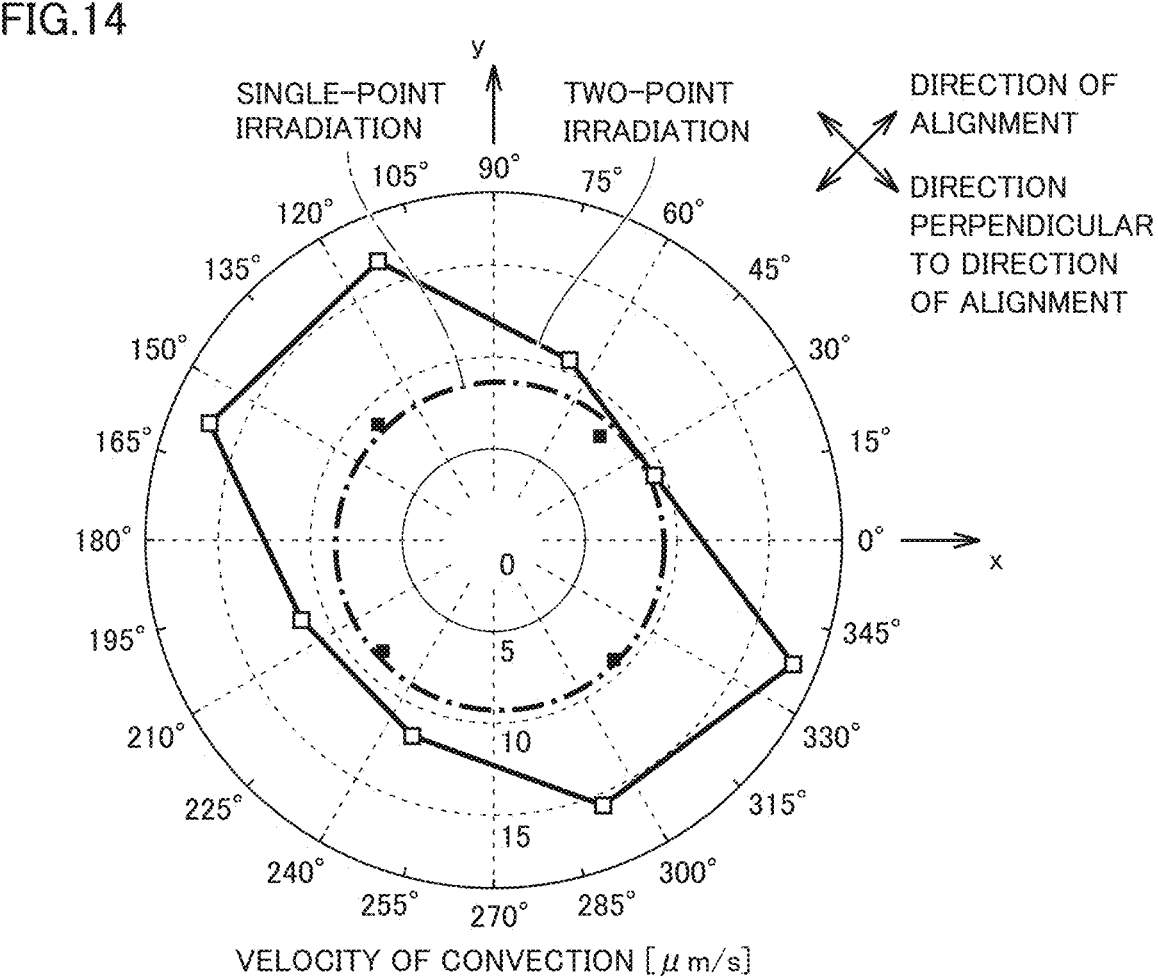
FIG. 14 is a diagram collectively showing velocities of resin beads carried by convection in a result of an experiment shown in FIG. 13.

FIG. 14 is a diagram collectively showing velocities of resin beads R carried by convection in a result of the experiment shown in FIG. 13. FIG. 14 shows an orientation and magnitude of a velocity of resin beads R carried by convection on a polar coordinate. The origin of the polar coordinate coincides with the center of each image shown in FIG. 13. A polar angle is determined such that the x direction shown in FIG. 13 points to 0° and the y direction points to 90°. A length of a polar radius represents an average velocity a velocity of convection) (unit of μm/s) of resin beads R obtained by conducting experiments a plurality of times. As a distance from the origin on the polar coordinate is longer, the velocity of convection is higher.

A direction from 45° to 225° in the figure in which two microbubbles MB1 and MB2 are aligned is called a "direction of alignment." A direction from 135° to 315° in the figure is called a "direction perpendicular to the direction of alignment." In the direction of alignment, the velocity of convection produced in two-point irradiation was approximately as high as the velocity of convection produced in single-point irradiation. In contrast, in the direction perpendicular to the direction of alignment, the velocity of convection produced in two-point irradiation was approximately 1.5 time as high as the velocity of convection produced in single-point irradiation.

Thus, in the present embodiment in which two-point irradiation is carried out, resin beads R can highly efficiently be collected in the region between two microbubbles MB1 and MB2 by enhancing convection along the direction perpendicular to the direction of alignment.

<Marangoni Convection>

In explanation of the mechanism for collecting resin beads R with reference to FIGS. 7 and 8, heat convection is explained as being produced by irradiation with light. Among types of heat convection, in particular, Marangoni convection based on a difference in interfacial tension may have been produced. More specifically, in general, interfacial tension generated at a gas-liquid interface has temperature dependency, and as the temperature of the gas-liquid interface is higher, interfacial tension is weaker. Therefore, when a temperature distribution at the gas-liquid interface is not uniform, a high-temperature region in the gas-liquid interface is pulled toward a low-temperature region such that interfacial tension is balanced. Motion of the gas-liquid interface at this time is transmitted to the inside of a liquid (bulk) and Marangoni convection may be produced. In the present embodiment as well, due to a temperature gradient caused by the photothermal effect, a difference in interfacial tension is produced at the surface of each of two microbubbles MB1 and MB2 and consequently Marangoni convection may be produced.

Figure 15:
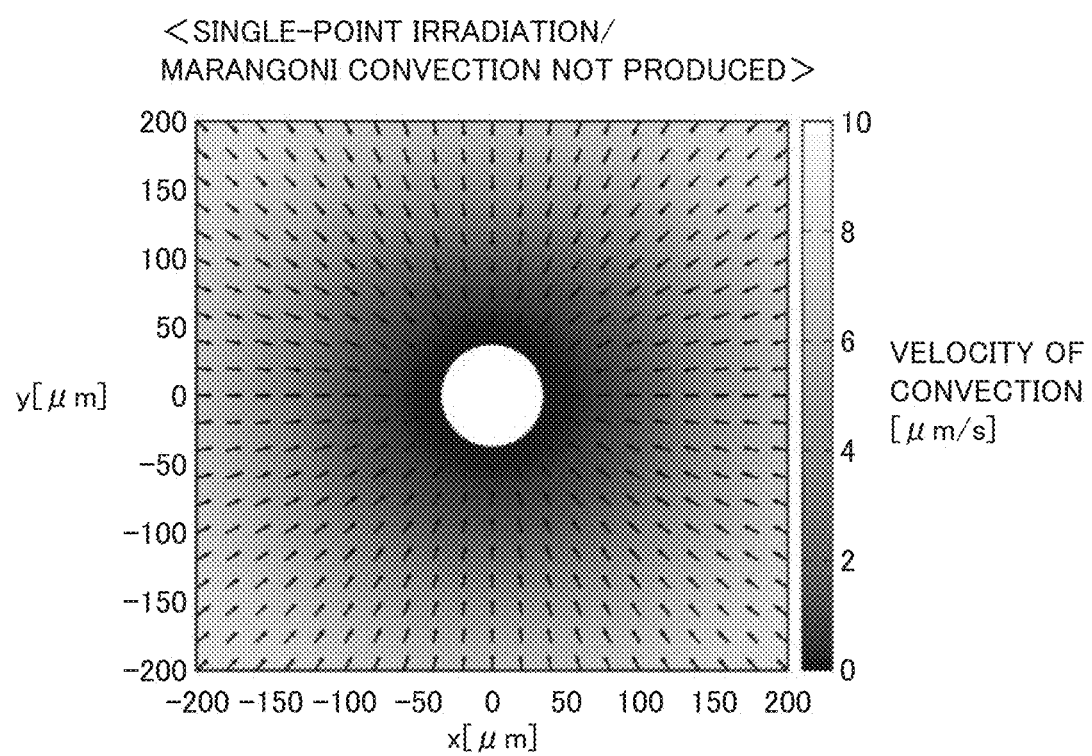
FIG. 15 is a diagram showing a convection simulation result when it is assumed that no Marangoni convection is produced in single-point irradiation.
Figure 16:
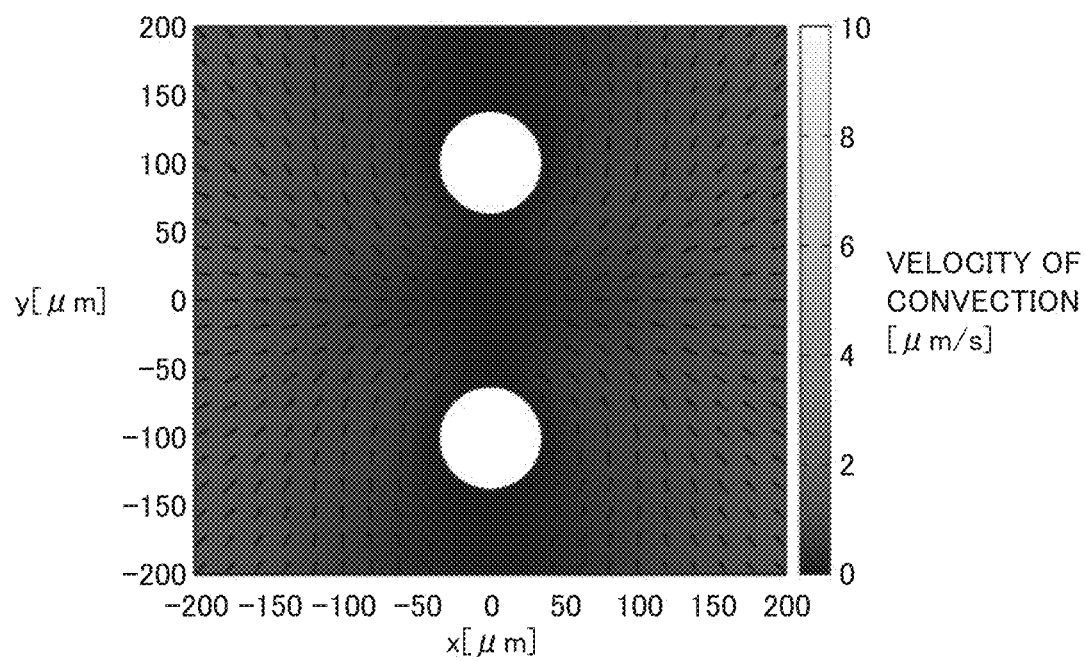
FIG. 16 is a diagram showing a convection simulation result when it is assumed that no Marangoni convection is produced in two-point irradiation.
Figure 17:
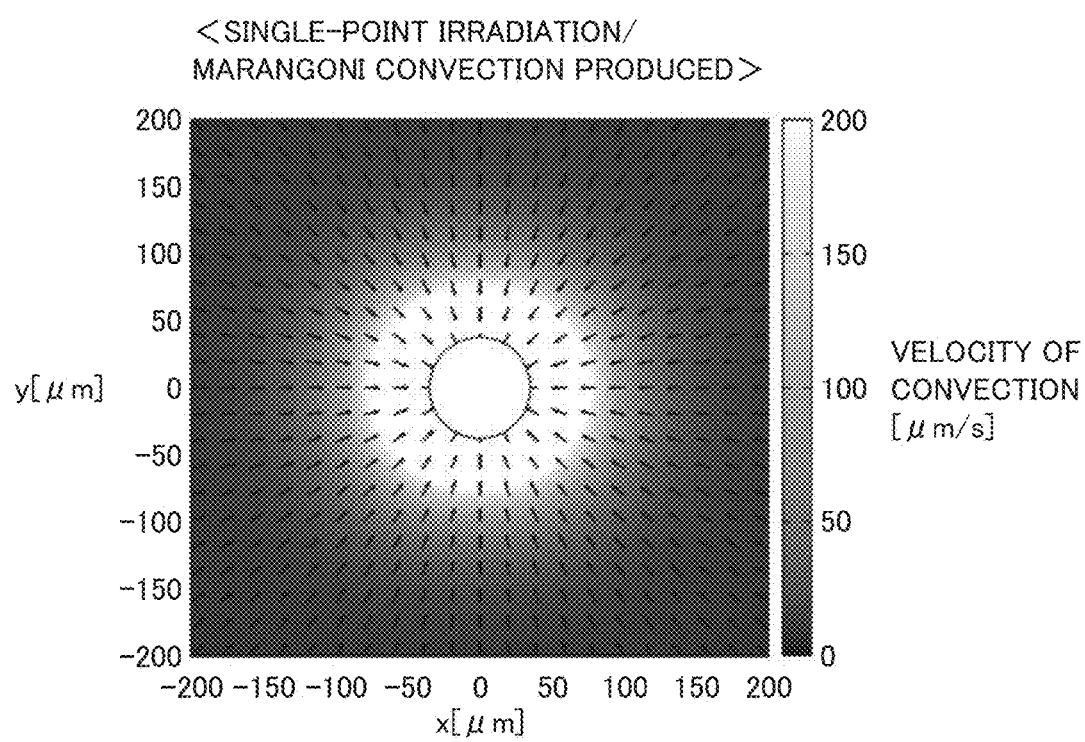
FIG. 17 is a diagram showing a convection simulation result when it is assumed that Marangoni convection is produced in single-point irradiation.
Figure 18:
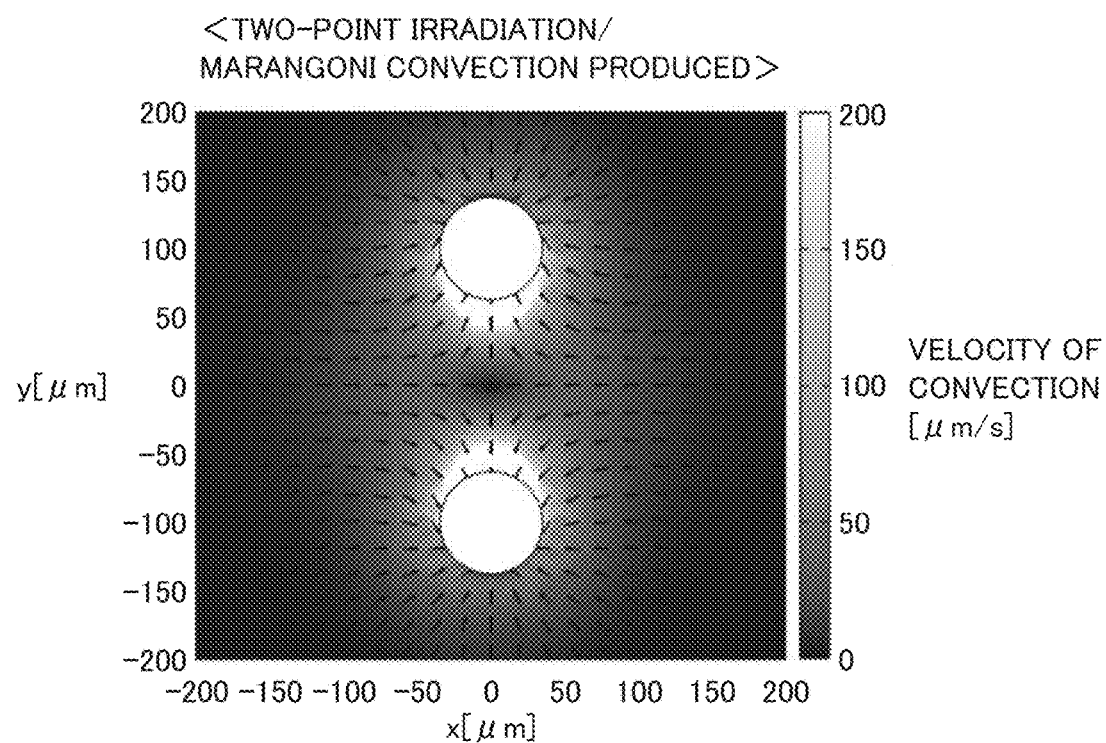
FIG. 18 is a diagram showing a convection simulation result when it is assumed that Marangoni convection is produced in two-point irradiation.

FIG. 15 is a diagram showing a convection simulation result when it is assumed that no Marangoni convection is produced in single-point irradiation. FIG. 16 is a diagram showing a convection simulation result when it is assumed that no Marangoni convection is produced in two-point irradiation. FIG. 17 is a diagram showing a convection simulation result when it is assumed that Marangoni convection is produced in single-point irradiation. FIG. 18 is a diagram showing a convection simulation result when it is assumed that Marangoni convection is produced in two-point irradiation. Simulation of convection is derived based on the finite element method.

In FIGS. 15 to 18, an orientation of an arrow represents an orientation of convection in a plane located 1 μm above upper surface US (the surface of thin film 12) of collection kit 10. A length of the arrow is the same regardless of a velocity of convection. The velocity of convection is represented by a gray scale in the background of the arrow, rather than the length of the arrow. As the background is whiter, the velocity of convection is higher (see a scale bar on the right in each figure).

Even when it is assumed that no Marangoni convection is produced, a result of production of convection toward a portion between two microbubbles MB1 and MB2 is obtained. The velocity of convection, however, is low (see FIG. 16). When production of Marangoni convection is assumed, on the other hand, the velocity of convection toward the portion between two microbubbles MB1 and MB2 is higher by approximately one order of magnitude than when it is assumed that no Marangoni convection is produced (see FIG. 18). A behavior of convection reproduced in this simulation well matches with a behavior of convection estimated from the actual measurement image shown in FIG. 13. Therefore, it is suggested that a large number of microscopic objects are collected between two microbubbles MB1 and MB2 under the influence of Marangoni convection.

<Collection of Bacteria>

In order to meet demands to more efficiently collect microscopic objects, output of laser beams L1 and L2 may be increased, because the velocity of convection is expected to be higher thereby. With increase in optical output, however, temperature increase in the vicinity of the laser spot also increases. Some microscopic objects require suppression of thermal damage thereto. For example, since many microorganisms are vulnerable to heat, they may be killed when a temperature is excessive due to irradiation with light. Therefore, microscopic objects are desirably highly efficiently collected while thermal damage thereto is suppressed. An example in which microorganisms (more specifically, bacteria) are collected will be described below. A collection kit 20 different in configuration from collection kit 10 shown in FIGS. 4 and 5 is employed in collecting bacteria.

Figure 19:
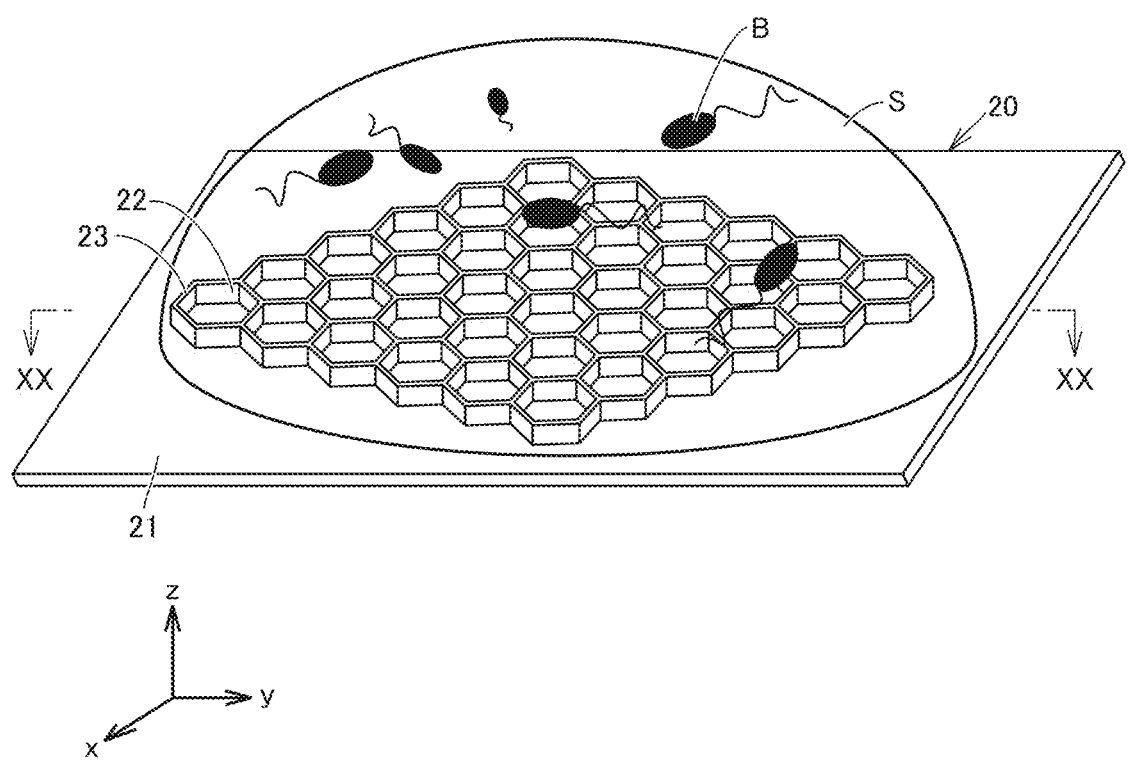
FIG. 19 is a perspective view schematically showing a configuration of another collection kit.

FIG. 19 is a perspective view schematically showing a configuration of another collection kit 20. FIG. 20 is a cross-sectional view of collection kit 20 along the line XX-XX in FIG. 19. FIG. 20 does not show sample S. Referring to FIGS. 19 and 20, collection kit 20 includes a substrate 21, a honeycomb polymeric film 22, and a thin film 23.

For example, cover glass is employed as substrate 21. Honeycomb polymeric film 22 is formed on substrate 21. Honeycomb polymeric film 22 is a polymeric film in which a honeycomb structure body is formed. A resin is employed as a material for honeycomb polymeric film 22. Thin film 23 is further formed on honeycomb polymeric film 22.

Thin film 23 is composed of a material that converts light energy into thermal energy by absorbing laser beams L1 and L2, similarly to thin film 12 (see FIGS. 4 and 5) formed in collection kit 10. In the present embodiment, thin film 23 is a gold thin film having a thickness of the nanometer order (specifically, for example, from 40 nm to 50 nm). Thin film 23 has a honeycomb structure with the structure of honeycomb polymeric film 22 being reflected. Therefore, a plurality of pores 24 in which bacteria B are caught and a plurality of partition walls 25 each serving as a partition between adjacent pores of the plurality of pores 24 are formed in thin film 23 (see PTL 2 for a detailed configuration of honeycomb collection kit 20).

*Pseudomonas aeruginosa* is employed as bacteria B in the present embodiment. *Pseudomonas aeruginosa* is *bacillus*. *Pseudomonas aeruginosa* typically has a major axis having a length of approximately 2 μm and a short axis having a length of approximately 0.5 μm. *Pseudomonas aeruginosa* is gram-negative bacteria.

Figure 21:
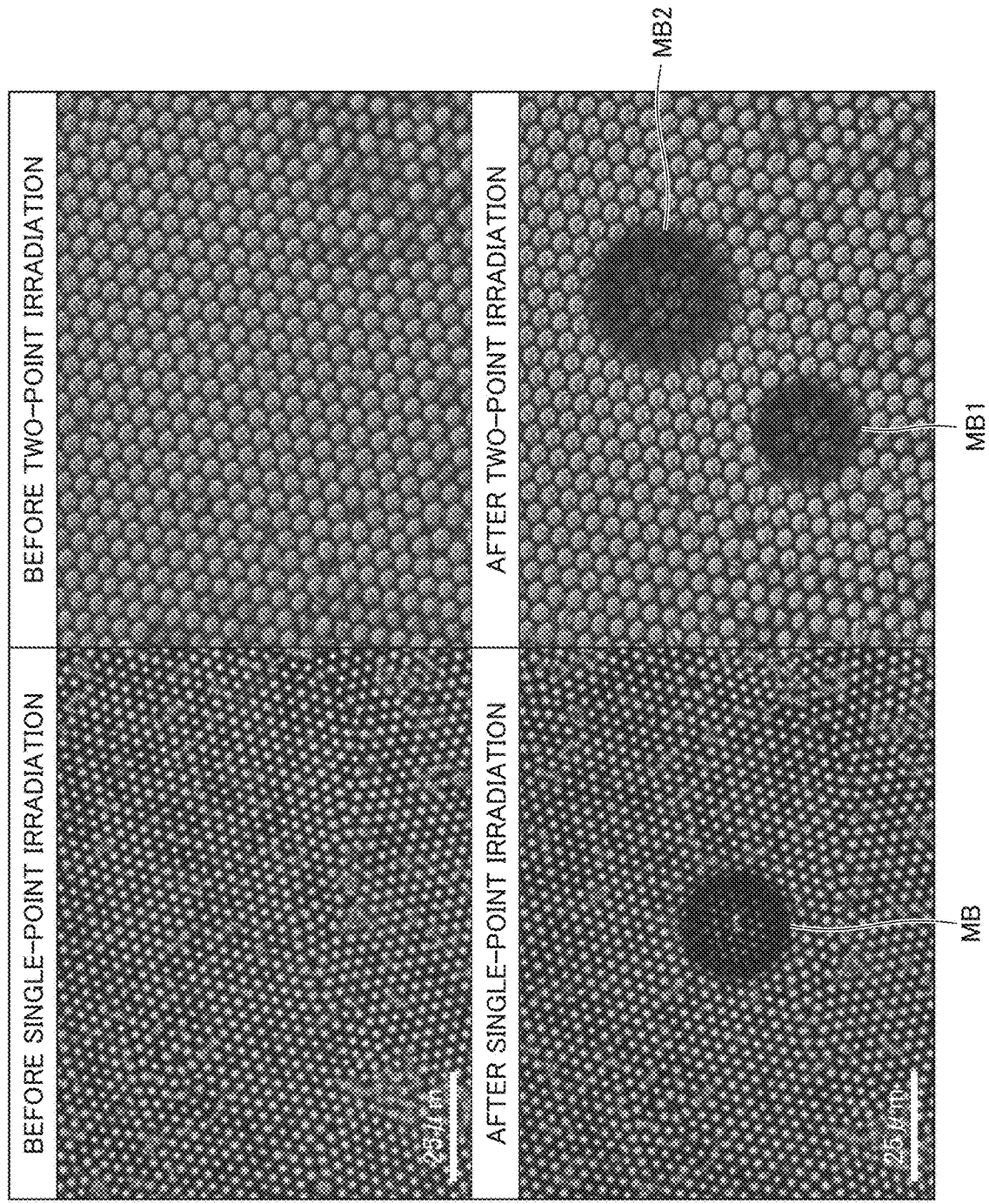
FIG. 21 is a diagram showing a perspective image of a honeycomb polymeric film in single-point irradiation and two-point irradiation.

FIG. 21 is a diagram showing a perspective image of honeycomb polymeric film 22 in single-point irradiation and two-point irradiation. The figure shows on the left, honeycomb polymeric film 22 before and after start of single-point irradiation, and shows on the right, honeycomb polymeric film 22 before and after start of two-point irradiation. Timing to start two-point irradiation was the same also in this example.

Output of laser beam L1 that passed through collection kit 20 in single-point irradiation was 15 mW. Output of laser beams L1 and L2 that passed through collection kit 20 in two-point irradiation was each 7.5 mW. Spot interval G was set to 60 μm. Objective lens 6 was of forty magnifications. A time period for irradiation with light was set to twenty seconds.

Microbubble MB2 produced in two-point irradiation was larger than microbubble MB1. In other words, the microbubble grew larger in irradiation with laser beam L2 having a wavelength of 800 nm than in irradiation with laser beam L1 having a wavelength of 1064 nm. This may be because of wavelength dependency of absorbance of honeycomb polymeric film 22.

A result of determination as to whether bacteria B collected by irradiation with light were alive or dead based on fluorescent staining of bacteria B will now be described. In the present embodiment, SYTO®9 and propidium iodide (PI) were employed as fluorescent dyes. SYTO®9 is a DNA dyeing reagent having membrane permeability, and it dyes DNA regardless of whether or not a cell membrane of bacteria (an outer membrane of *Pseudomonas aeruginosa* representing gram-negative bacteria) has been damaged. In other words, SYTO®9 dyes both of viable bacteria (viable bacteria) and dead bacteria (killed bacteria). As bacteria containing SYTO®9 were irradiated with light at an excitation wavelength for SYTO®9, bacteria emit green fluorescence. On the other hand, PI does not have membrane permeability. Therefore, only bacteria (killed bacteria) having the cell membrane damaged were dyed with PI. When PI was externally excited, it emitted red fluorescence.

Figure 22:
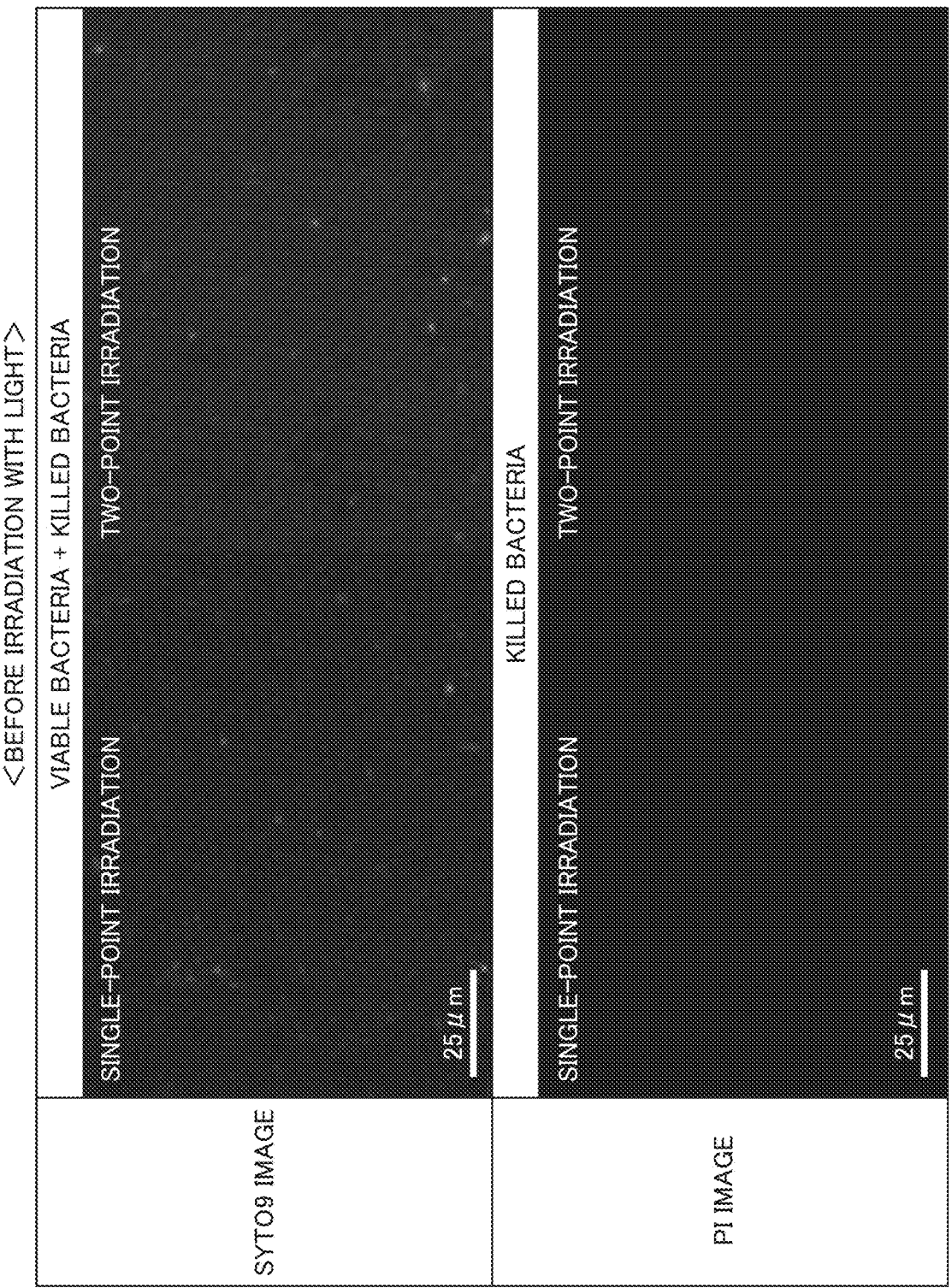
FIG. 22 is a diagram showing a fluorescence observation image before irradiation with light.
Figure 23:
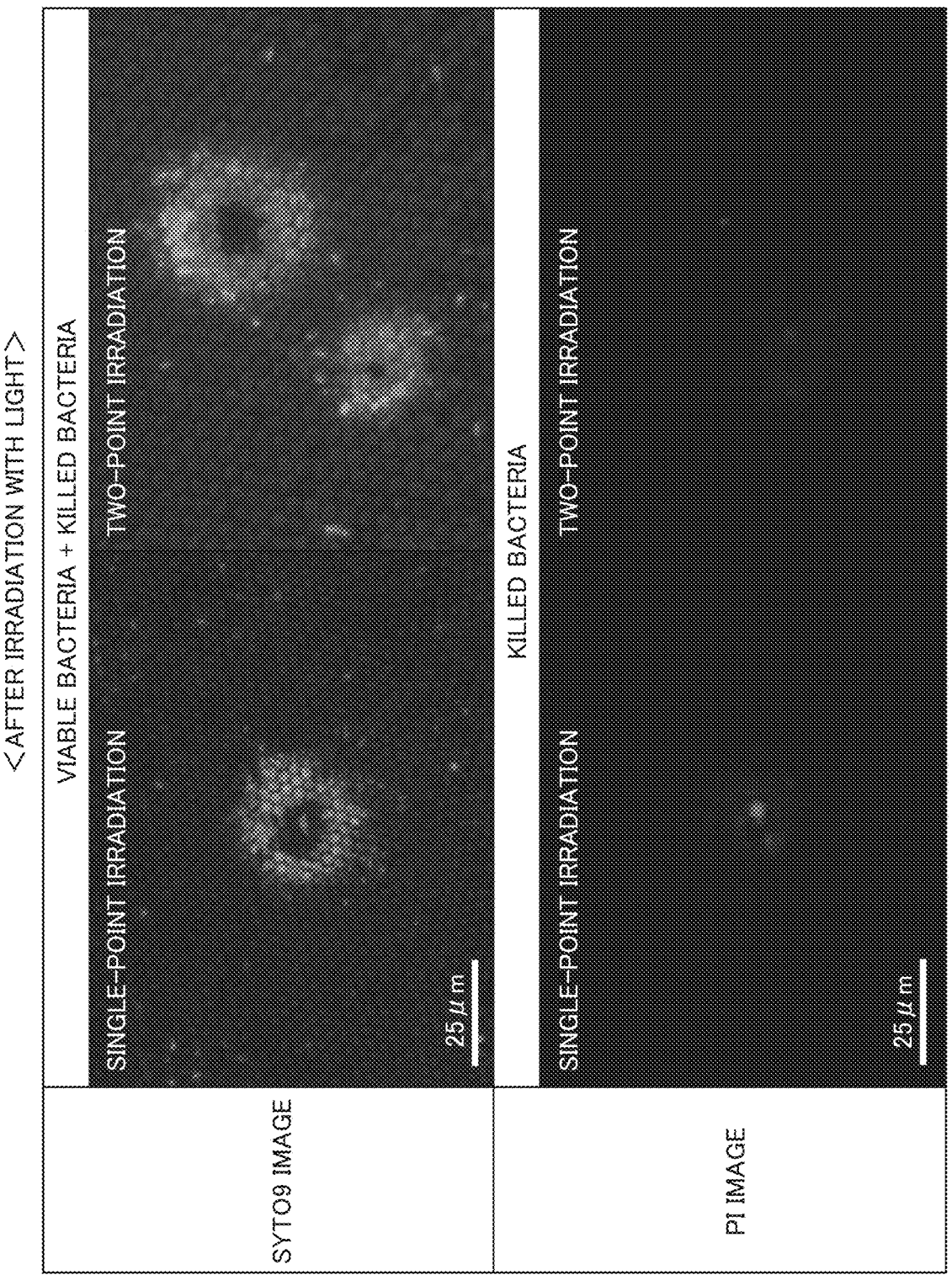
FIG. 23 is a diagram showing a fluorescence observation image after irradiation with light.

FIG. 22 is a diagram showing a fluorescence observation image before irradiation with light. FIG. 23 is a diagram showing a fluorescence observation image after irradiation with light. A fluorescence observation image obtained at an excitation wavelength for SYTO®9 (which is also denoted as a "SYTO®9 image") is shown in an upper part of FIGS. 22 and 23. A fluorescence observation image obtained at an excitation wavelength for PI (which is also denoted as a "PI image") is shown in a lower part of FIGS. 22 and 23.

In the SYTO®9 image after irradiation with light, fluorescence was observed around laser spots in results in each of single-point irradiation and two-point irradiation. It was thus found that bacteria B were collected around the laser spots and caught in pores 24 in each of single-point irradiation and two-point irradiation. Based on comparison between results in single-point irradiation and results in two-point irradiation, an area of fluorescence in two-point irradiation was larger than an area of fluorescence in single-point irradiation. This results also supports the fact that an area where bacteria B were collected was larger, that is, a larger number of bacteria B were collected, in two-point irradiation.

Based on comparison of the PI images after irradiation with light between single-point irradiation and two-point irradiation, it was found that a survival rate of bacteria B was higher in two-point irradiation than in single-point irradiation because an amount of observed bacteria (that is, an amount of killed bacteria) was smaller. It was thus confirmed that two-point irradiation can suppress thermal damage to bacteria B as compared with single-point irradiation. This may be because, under a laser output condition described previously, output of each of laser beams L1 and L2 in two-point irradiation was half that of laser beam L1 in single-point irradiation and temperature increase at the laser spot was less in two-point irradiation.

Figure 24:
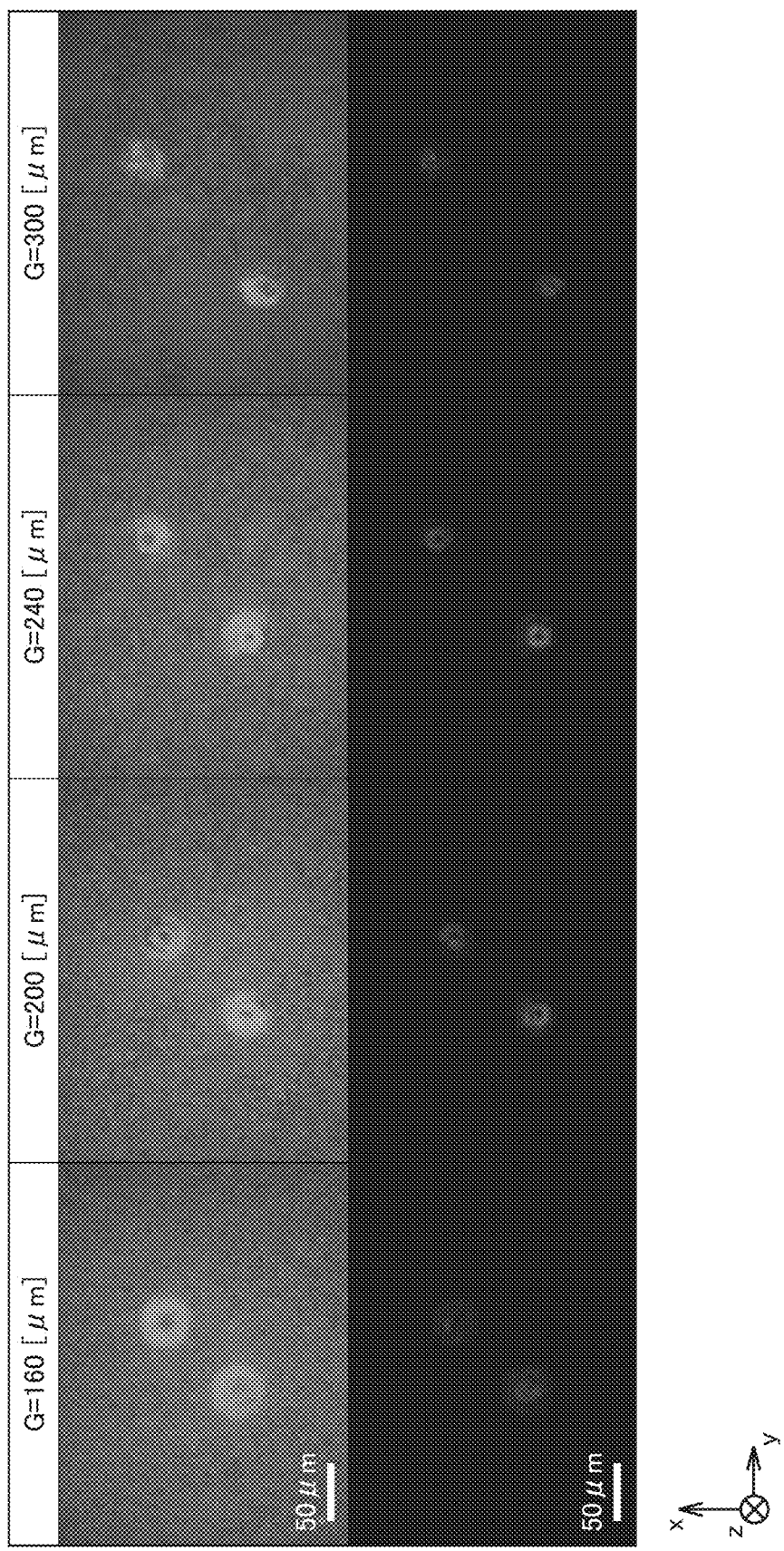
FIG. 24 is a diagram showing a fluorescence observation image with a spot interval G in two-point irradiation being varied.

FIG. 24 is a diagram showing a fluorescence observation image with spot interval G in two-point irradiation being varied. In FIG. 24, with spot interval G being varied in four ways as in FIG. 12, a SYTO®9 image and a PI image were obtained and a result of collection of bacteria B was checked. Output of laser beams L1 and L2 that passed through collection kit 20 was each 20 mW. Objective lens 6 was of ten magnifications. A time period for irradiation with light was set to twenty seconds.

In the SYTO®9 image (above), collection of bacteria B was confirmed in each case of four spot intervals G. In the PI image (below), strong fluorescence was observed in all cases of spot intervals G, and it was also confirmed that the survival rate of bacteria B was high.

Figure 25:
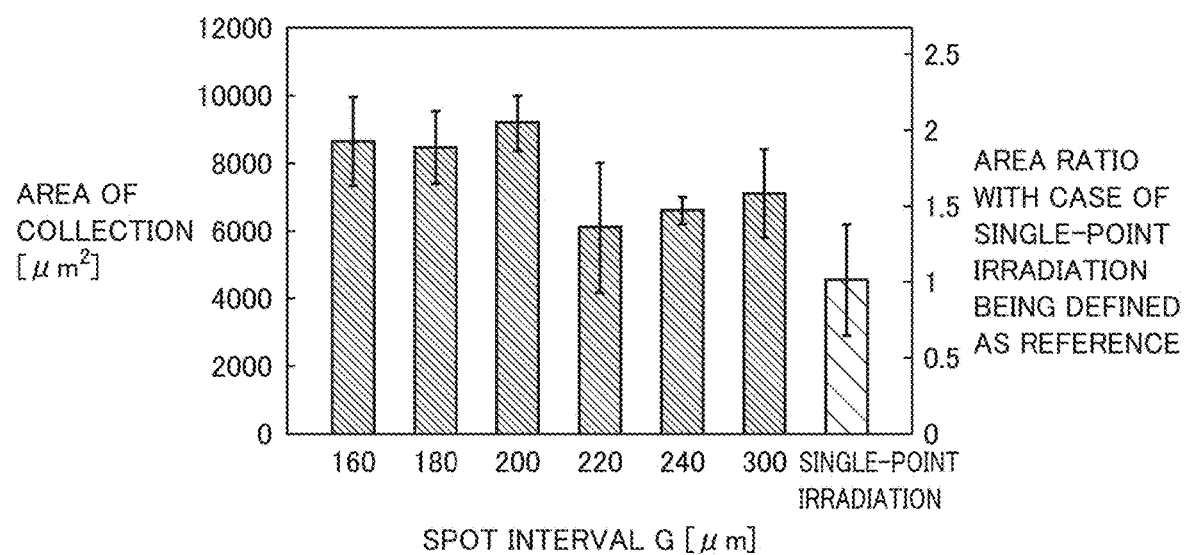
FIG. 25 is a diagram showing dependency on a spot interval, of a result of collection of bacteria B by two-point irradiation.

FIG. 25 is a diagram showing dependency on a spot interval, of a result of collection of bacteria B by two-point irradiation. In FIG. 25, the abscissa represents spot interval G. The ordinate on the left represents an area of collected bacteria B. The ordinate on the right represents a ratio of an area of collected bacteria B in two-point irradiation with an area of collected bacteria B in single-point irradiation being defined as the reference. At the right end of the abscissa, a result in single-point irradiation is shown for comparison. A condition in two-point irradiation is the same as the condition described with reference to FIG. 24. Output of laser beam L1 in single-point irradiation was 40 mW.

Referring to FIG. 25, an area of collected bacteria B in two-point irradiation in which spot interval G was set to 160 μm to 200 μm was approximately 1.5 time to 2.0 times as large as the area of collected bacteria B in single-point irradiation. When spot interval G was equal to or larger than 220 μm, the area of collected bacteria B became relatively small, however, it was also confirmed that the area was still larger than the area of collected bacteria B in single-point irradiation.

As set forth above, in the first embodiment, two microbubbles MB1 and MB2 are produced by two-point irradiation and convection along the specific direction perpendicular to the direction of alignment of microbubble MB1 and microbubble MB2 is produced. Owing to this convection, a plurality of microscopic objects dispersed in sample S are drawn in between two microbubbles MB1 and MB2 and collected in the stagnation region between two microbubbles MB1 and MB2. As clarified by the present inventors based on the actual measurement image and simulation of convection, convection in the specific direction is significantly enhanced in two-point irradiation (see FIGS. 13 to 18). By using this phenomenon, in each case of a flat gold thin film and a honeycomb structure body having a gold thin film formed on its surface, more microscopic objects can be collected in two-point irradiation than in single-point irradiation even though output of each laser beam is low (even though laser output is half in the example described previously). Therefore, according to the first embodiment, microscopic objects can highly efficiently be collected while thermal damage to microscopic objects is suppressed.

Second Embodiment

In the first embodiment, two-point irradiation in which collection kit 10 is irradiated with laser beams L1 and L2 emitted from two light sources (laser apparatuses 401 and 402) is described by way of example. So long as a plurality of beams of laser are emitted, a single light source of laser beams may be applicable. A plurality of beams of laser should only be emitted, and three or more beams can also be emitted (multi-point irradiation). In a second embodiment, a configuration in which collection kit 10 is irradiated with a large number of laser beams emitted from a single laser module will be described.

Figure 26:
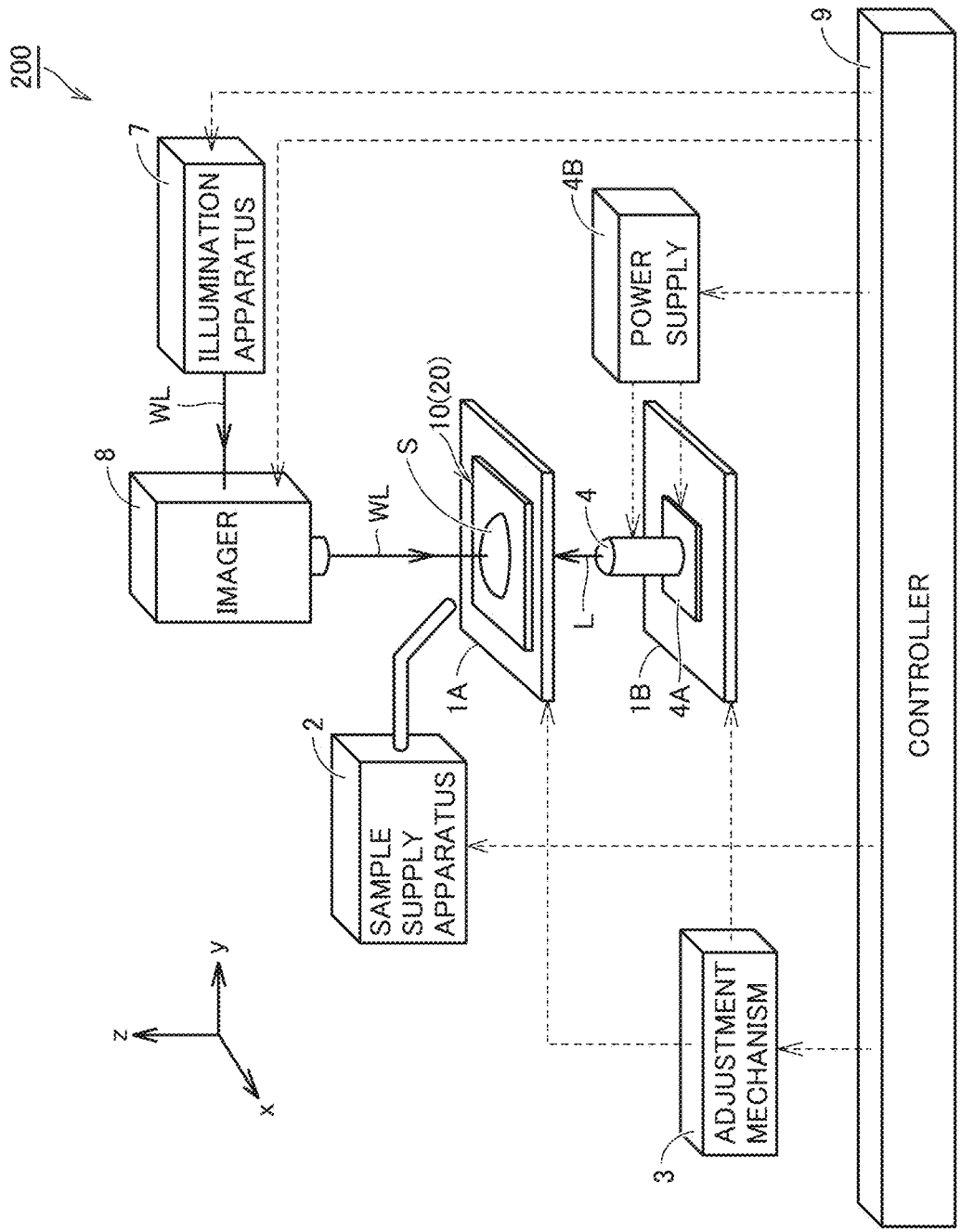
FIG. 26 is a diagram schematically showing an overall configuration of a microscopic object collection system according to a second embodiment.

FIG. 26 is a diagram schematically showing an overall configuration of a microscopic object collection system 200 according to the second embodiment. Referring to FIG. 26, collection system 200 is different from collection system 100 according to the first embodiment (see FIG. 1) in two points below. Firstly, collection system 200 includes a laser module 4, a cooling apparatus 4A, and a power supply 4B instead of laser apparatuses 401 and 402 and objective lens 6. Secondly, collection system 200 includes a sample stage 1A and a light source stage 1B instead of XYZ-axis stage 1.

Sample stage 1A is an XYZ-axis stage and configured to be movable in the x direction, the y direction, and the z direction. Sample stage 1A holds collection kit 10 similarly to XYZ-axis stage 1.

Light source stage 1B is an XYZ-axis stage and configured to be movable in the x direction, the y direction, and the z direction. Light source stage 1B holds laser module 4 and cooling apparatus 4A.

Laser module 4 is a semiconductor laser module that emits a large number of laser beams in response to an instruction from controller 9. A configuration of laser module 4 will be described in detail with reference to FIGS. 27 and 28.

Cooling apparatus 4A cools laser module 4. Laser module 4 can be compact by employing a Peltier element (not shown) as cooling apparatus 4A. Cooling apparatus 4A does not have to be provided when an energy-saving laser light source (laser module 4) is employed.

Power supply 4B supplies a current for driving laser module 4. Power supply 4B supplies electric power for driving cooling apparatus 4A.

Adjustment mechanism 3 is configured to adjust a position of sample stage 1A in the x direction, the y direction, and the z direction and to adjust a position of light source stage 1B in the x direction, the y direction, and the z direction, in response to an instruction from controller 9. In the second embodiment, in determining a position to be irradiated with light, a horizontal position (a position in the x direction and the y direction) of sample stage 1A is adjusted and a height (a position in the z direction) of light source stage 1B is adjusted. Relative positional relation between collection kit 10 mounted on sample stage 1A and laser module 4 provided on light source stage 1B is thus adjusted.

The configuration of adjustment mechanism 3 is not particularly limited so long as relative positional relation between collection kit 10 and laser module 4 can be adjusted. Adjustment mechanism 3 may adjust, for example, the position of collection kit 10 with respect to fixed laser module 4 or may adjust the position of laser module 4 with respect to fixed collection kit 10.

In the configuration shown in FIG. 26, white light WL emitted from illumination apparatus 7 is guided to imager 8, for example, through optical fibers (not shown), and emitted from imager 8 toward a portion of imaging in the vicinity of a laser spot.

Figure 27:
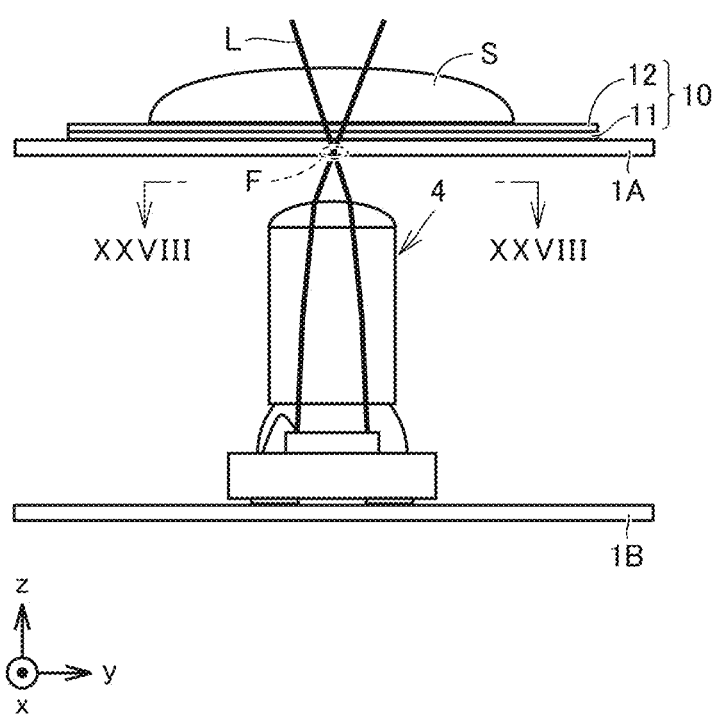
FIG. 27 is a diagram showing an optical system of the microscopic object collection system according to the second embodiment.

FIG. 27 is a diagram showing an optical system of microscopic object collection system 200 according to the second embodiment. Referring to FIG. 27, laser module 4 is provided on light source stage 1B and arranged below sample stage 1A. Collection kit 10 (which may be collection kit 20) is provided on sample stage 1A. Collection kit 10 on sample stage 1A is irradiated with a large number of laser beams L emitted upward from laser module 4. Cooling apparatus 4A is not shown in FIG. 27.

Figure 28:
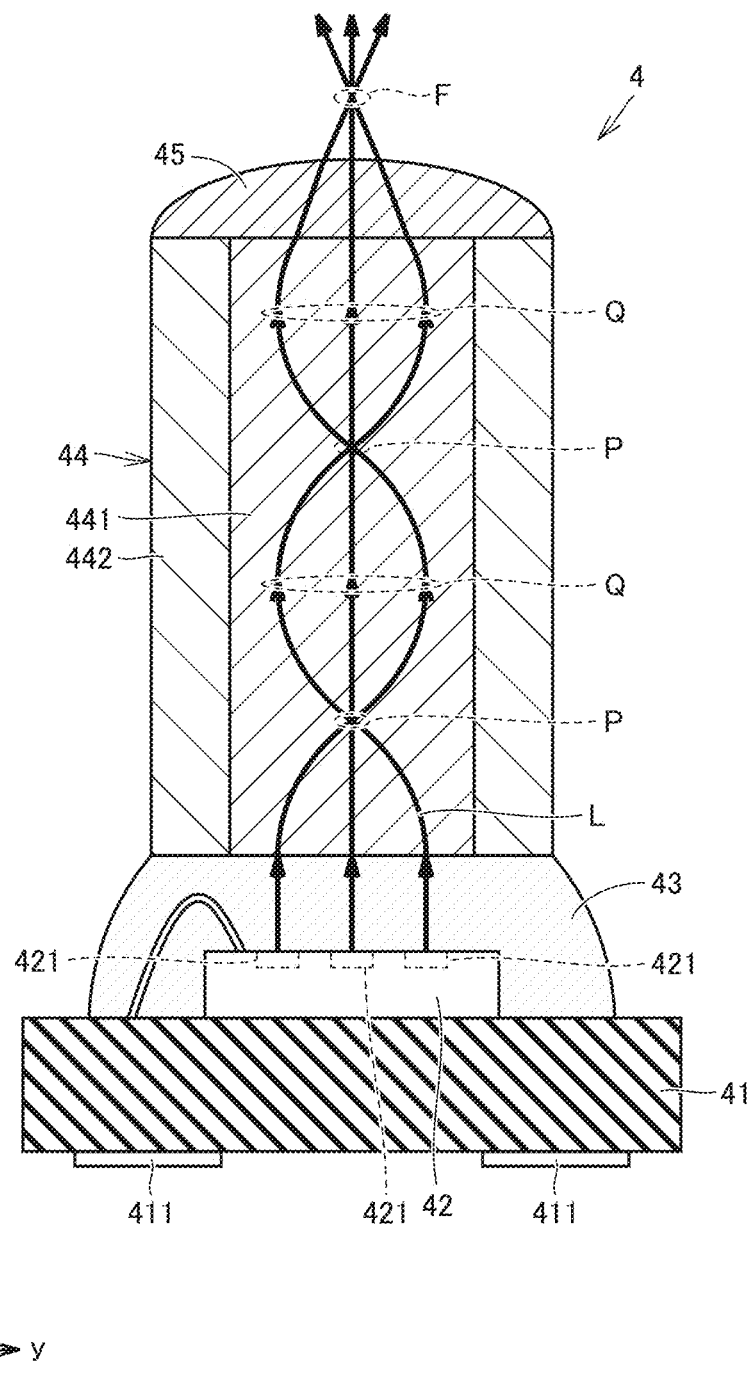
FIG. 28 is a cross-sectional view of a laser module along the line XXVIII-XXVIII in FIG. 27.

FIG. 28 is a cross-sectional view of laser module 4 along the line XXVIII-XXVIII in FIG. 27. Referring to FIG. 28, laser module 4 includes a substrate 41, a surface emission element 42, a joint member 43, an optical waveguide 44, and a lens 45.

Substrate 41 is a flat plate formed of an insulating material, and it is, for example, a printed circuit board or a ceramic substrate. Surface emission element 42 is mounted on a surface of substrate 41. An electrode 411 is formed on a rear surface of substrate 41. Electrode 411 is electrically connected to surface emission element 42, for example, by wire bonding. A drive current is supplied to surface emission element 42 from power supply 4B (see FIG. 26) through electrode 411.

Surface emission element 42 is array-type vertical cavity surface emitting laser (VCSEL). Surface emission element 42 includes a plurality of (for example, thirty) light emission regions 421 disposed in an array. All light emission regions 421 simultaneously emit light and emits, for example, near infrared laser beams L. Laser beams L go out in a direction perpendicular to a surface of surface emission element 42 (upward in the z direction).

For example, an adhesive is employed as joint member 43, and joins optical waveguide 44 onto surface emission element 42. Joint member 43 is made of a material transparent to light (near infrared light in this example) emitted from surface emission element 42.

Optical waveguide 44 condenses a plurality of laser beams L emitted from surface emission element 42. A material for optical waveguide 44 is, for example, a resin or glass. Optical waveguide 44 includes a core 441 and a clad 442.

Core 441 is in a columnar shape. An incident end of core 441 is formed to cover all light emission regions 421 included in surface emission element 42 such that all laser beams L emitted from surface emission element 42 are incident thereto. Clad 442 is in a cylindrical shape. Clad 442 is formed to cover a side surface of core 441.

Lens 45 is a plano convex lens including a plane and a convex surface. The plane of lens 45 is joined to an emission end of optical waveguide 44. The convex surface of lens 45 protrudes in a direction of emission of light from an emission portion of laser module 4.

A path of propagation of laser beams L in laser module 4 configured as above will be described. Optical waveguide 44 is a graded-index (GI) optical fiber. Therefore, an index of refraction of core 441 of optical waveguide 44 is highest at the center in a radial direction of core 441 and smoothly lowers toward radially outside. Laser beams L that propagate through the inside of core 441 have a plurality of modes different from each other in propagation distance. Light in a lower-order mode advances through the center of the core and light in a higher-order mode advances as being displaced from the center of the core. Though a propagation distance of light in the lower-order mode is short, a speed of propagation of light in the lower-order mode is relatively low due to the high index of refraction at the center of the core. In contrast, light in the higher-order mode is long in propagation distance whereas it is relatively high in propagation speed. A distribution of the index of refraction of core 441 is designed such that a difference in propagation time period between the modes is sufficiently small.

The plurality of laser beams L that propagate through the inside of core 441 having such a distribution of the index of refraction form a node P and an antinode Q. Positions of node P and antinode Q may vary depending on a wavelength of laser beams L. In connection with a direction in which laser beams L travel (the z direction in the figure), a length of optical waveguide 44 is determined such that the emission end of optical waveguide 44 is not located at a position somewhere between node P and antinode Q. In other words, the length of optical waveguide 44 is determined such that the emission end of optical waveguide 44 is located somewhere between antinode Q and node P as shown in FIG. 28 or the emission end of optical waveguide 44 coincides with antinode Q. Consequently, the plurality of laser beams L that have propagated through optical waveguide 44 are emitted from the emission end of optical waveguide 44 with the tendency of being condensed. The plurality of emitted laser beams L are further condensed to an identical location by lens 45 to form a single focal point F.

Referring again to FIG. 27, adjustment mechanism 3 is configured to adjust the height (the position in the z direction) of light source stage 1B on which laser module 4 is carried in response to an instruction from controller 9 as described previously. In the present embodiment, controller 9 adjusts the height of light source stage 1B such that the position in the z direction of collection kit 10 is above focal point F.

A plurality of laser beams L emitted upward from the convex surface of lens 45 are separate from one another in the vicinity of lens 45, however, they intersect with one another thereabove to form focal point F. Then, the plurality of laser beams L are again separate from one another further above focal point F. Therefore, by arranging collection kit 10 above focal point F, collection kit 10 is irradiated with a plurality of laser beams L (thirty laser beams in this example). In other words, multi-point irradiation of collection kit 10 is realized.

An interval (spot interval G) between the plurality of laser beams L is larger upward above focal point F. Therefore, by adjusting the position in the z direction of XYZ-axis stage 1, spot interval G can also be set as appropriate. The spot interval can thus be adjusted as described in the first embodiment and the number of collected microscopic objects by irradiation with a plurality of laser beams L can be increased.

According to the second embodiment, microscopic objects can highly efficiently be collected while thermal damage to the microscopic objects is suppressed as in the first embodiment.

Furthermore, in laser module 4, a large number of laser light sources and a condensing lens are integrally formed. By thus packaging (modularizing) laser module 4, collection system 200 can be compacter than collection system 100 (see FIG. 1) in which laser apparatuses 401 and 402 and objective lens 6 are individually constructed. Utilizing such a characteristic as being compact, a plurality of laser modules 4 may be disposed in an array. By providing a microarray in which a plurality of collection kits 10 (or a plurality of collection kits 20) are disposed in an array above the laser module, collection of microscopic objects in each collection kit 10 can simultaneously proceed. Consequently, microscopic objects can be collected in a shorter period of time.

It should be understood that the embodiments disclosed herein are illustrative and non-restrictive in every respect. The scope of the present disclosure is defined by the terms of the claims rather than the description of the embodiments above and is intended to include any modifications within the scope and meaning equivalent to the terms of the claims.

REFERENCE SIGNS LIST

1 XYZ-axis stage; 1A sample stage; 1B light source stage; 2 sample supply apparatus; 3 adjustment mechanism; 401, 402 laser apparatus; 4 laser module; 4A cooling apparatus; 4B power supply; 41 substrate; 411 electrode; 42 surface emission element; 421 light source; 43 joint member; 44 optical waveguide; 441 core; 442 clad; 5 optical component; 6 objective lens; 7 illumination apparatus; 8 imager; 9 controller; 10, 20 collection kit; 11 substrate; 12 thin film; 21 substrate; 22 honeycomb polymeric film; 23 thin film; 24 pore; 25 partition wall; 100, 200, 900 collection system

The invention claimed is:

1. A microscopic object collection method of collecting a plurality of microscopic objects dispersed in a liquid, the method comprising:
preparing the liquid on a photothermal conversion region provided on a main surface of a substrate;
irradiating the photothermal conversion region with a first beam and a second beam with the first beam and the second beam being distant from each other, the first beam and the second beam each being a beam having a wavelength within an absorption wavelength range of the photothermal conversion region;
producing a first bubble in the liquid at a first position of the photothermal conversion region irradiated with the first beam and producing a second bubble in the liquid at a second position of the photothermal conversion region irradiated with the second beam by heating the liquid by irradiation with the first and second beams; and
collecting the plurality of microscopic objects in a region of the liquid between the first bubble and the second bubble by producing convection of the liquid in a specific direction, the first bubble and the second bubble being aligned in a direction of alignment, the specific direction being a direction in parallel to the main surface and perpendicular to the direction of alignment of the first bubble and the second bubble; wherein
the photothermal conversion region includes a material that includes a light absorption factor in the wavelength range of the first and second beams.

2. The microscopic object collection method according to claim 1, wherein
the collecting the plurality of microscopic objects includes enhancing convection of the liquid along the specific direction such that a flow velocity of convection of the liquid along the specific direction is higher than a flow velocity of convection of the liquid along another direction by setting (i) output of the first and second beams and (ii) an interval between the first position irradiated with the first beam and the second position irradiated with the second beam, and
convection of the liquid along the another direction includes convection along the direction in parallel to the main surface and in parallel to the direction of alignment.

3. The microscopic object collection method according to claim 2, wherein
- the collecting the plurality of microscopic objects includes producing convection of the liquid along the specific direction and convection of the liquid along the another direction by setting the output and the interval such that the plurality of microscopic objects are collected in the liquid around each of the first bubble and the second bubble, and
- distribution of the plurality of microscopic objects collected around the first bubble is denser at a portion of the first bubble that faces the second bubble in the direction of alignment and
- distribution of the plurality of microscopic objects collected around the second bubble is denser at a portion of the second bubble that faces the first bubble in the direction of alignment.

4. The microscopic object collection method according to claim 2, wherein
- the output and the interval are able to be calculated by values including a spot diameter of the first beam, a spot diameter of the second beam, and an absorbance and thermal conductivity of the photothermal conversion region.

* * * * *